United States Patent [19]
Dorfmeister et al.

[11] Patent Number: 5,995,868
[45] Date of Patent: Nov. 30, 1999

[54] SYSTEM FOR THE PREDICTION, RAPID DETECTION, WARNING, PREVENTION, OR CONTROL OF CHANGES IN ACTIVITY STATES IN THE BRAIN OF A SUBJECT

[75] Inventors: Josef Dorfmeister; Mark Frei; David Lerner, all of Lawrence; Ivan Osorio, Leawood; John Ralston, Lawrence, all of Kans.

[73] Assignee: University of Kansas, Lawrence, Kans.

[21] Appl. No.: 08/778,771

[22] Filed: Jan. 6, 1997

Related U.S. Application Data

[60] Provisional application No. 60/010,477, Jan. 23, 1996.

[51] Int. Cl.$^6$ ................................................ A61B 5/04
[52] U.S. Cl. ........................ 600/544; 600/545; 600/300
[58] Field of Search ................................ 600/544, 300, 600/545, 546; 607/45

[56] References Cited

U.S. PATENT DOCUMENTS

| | | | |
|---|---|---|---|
| 3,850,161 | 11/1974 | Liss | 128/2.1 |
| 4,702,254 | 10/1987 | Zabara | 128/419 |
| 4,867,164 | 9/1989 | Zabara . | |
| 5,215,086 | 6/1993 | Terry et al. | 128/421 |
| 5,222,503 | 6/1993 | Ives et al. . | |
| 5,269,302 | 12/1993 | Swartz et al. . | |
| 5,269,303 | 12/1993 | Wernicke et al. . | |
| 5,299,569 | 4/1994 | Wernicke et al. | 607/45 |
| 5,349,962 | 9/1994 | Lockard et al. | 128/732 |
| 5,626,627 | 5/1997 | Krystal et al. | 607/45 |

OTHER PUBLICATIONS

Thomas L. Babb, Elmo Mariani and Paul H. Crandall; "An Electronic Circuit for Detection of EEG Seizures Recorded With Implanted Electrodes," Electroencephalography and Clinical Neurophysiology, (1974); vol. 37, pp. 305–308.

J. Gotman and P. Gloor; "Automatic Recognition and Quantification of Interictal Epileptic Activity in the Human Scalp EEG," Electroencephalography and Clinical Neurophysiology, (1976); vol. 41, pp. 513–529.

J. Gotman, J.R. Ives and P. Gloor; "Automatic Recognition of Inter–Ictal Epileptic Activity in Prolonged EEG Recordings," Electroencephalography and Clinical Neurophysiology, (1979); vol. 46, pp. 510–520.

Armand Siegel, Cheryl L. Grady and Allan F. Mirsky, "Prediction of Spike–Wave Bursts in Absence Epilepsy by EEG Power–Spectrum Signals," Epilepsia, (Feb., 1982); vol. 23, pp. 47–60.

J. Gotman; "Automatic Recognition of Epileptic Seizures in the EEG," Electroencephalography and Clinical Neurophysiology, (1982); vol. 54, pp. 530–540.

J. Gotman; "Automatic Seizure Detection: Improvements and Evaluation," Electroencephalography and Clinical Neurophysiology, (1990); vol. 76, pp. 317–324.

J,. Gotman and L.Y. Wang, "State–Dependent Spike Detection: Concepts and Preliminary Results," Electroencephalography and Clinical Neurophysiology, (1991); vol. 79, pp. 11–19.

(List continued on next page.)

*Primary Examiner*—William E. Kamm
*Assistant Examiner*—Eleni Mantis Mercader
*Attorney, Agent, or Firm*—Donald R. Schoonover

[57] ABSTRACT

A system (10) analyzes signals representative of a subject's brain activity in a signal processor (12) for information indicating the subject's current activity state and for predicting a change in the activity state. One preferred embodiment uses a combination of nonlinear filtering methods to perform real-time analysis of the electro-encephalogram (EEG) or electro-corticogram (ECoG) signals from a subject patient for information indicative of or predictive of a seizure, and to complete the needed analysis at least before clinical seizure onset. The preferred system then performs an output task for prevention or abatement of the seizure, or for recording pertinent data.

52 Claims, 15 Drawing Sheets

Microfiche Appendix Included
(1 Microfiche, 20 Pages)

OTHER PUBLICATIONS

Anthony M. Murro, Don W. King, Joseph R. Smith, Brian B. Gallagher, Herman F. Flanigin, and Kimford Meador; "Computerized Seizure Detection of Complex Partial Seizures," Electroencephalography and Clinical Neurophysiology, (1991); vol. 79, pp. 330–333.

E.A. Bartnik, K.J. Blinowska and P.J. Durka; "Single Evoked Potential Reconstruction by Means of Wavelet Transform," Biological Cybernetics, (1992); vol. 67, pp. 175–181.

Flavia Pauri, Francesco Pierelli, Gian–Emilio Chatrian and William W. Erdly; "Long–Term EEG–Video–Audio Monitoring: Computer Detection of Focal EEG Seizure Patterns," Electroencephalography and Clinical Neurophysiology, (1992); vol. 82, pp. 1–9.

J. Reiher, F. Grand'Maison and C.P. Leduc; "Partial Status Epilepticus: Short–Term Prediction of Seizure Outcome From On–Line EEG Analysis," Electroencephalography and Clinical Neurophysiology, (1992); vol. 82, pp. 17–22.

A. Liu, J.S. Hahn, G.P. Heldt and R.W. Coen; "Detection of Neonatal Seizures Through Computerized EEG Analysis," Electroencephalography and Clinical Neurophysiology, (1992); vol. 82, pp. 30–37.

Wayne E. Hostetler, Herbert J. Doller and Richard W. Homan; "Assessment of a Computer Program to Detect Epileptiform Spikes," Electroencephalography and Clinical Neurophysiology, (1992); vol. 83, pp. 1–11.

J. Gotman and Li–Yan Wang; "State Dependent Spike Detection: Validation," Electroencephalography and Clinical Neurophysiology, (1992); vol. 83, pp. 12–18.

Andrew J. Gabor and Masud Seyal; "Automated Interictal EEG Spike Detection Using Artificial Neural Networks," Electroencephalography and Clinical Neurophysiology, (1992); vol. 83, pp. 271–280.

P. Hilfiker and M. Egli; "Detection and Evolution of Rhythmic Components In Ictal EEG Using Short Segment Spectra and Discriminant Analysis," Electroencephalography and Clinical Neurophysiology, (1992) vol. 82, pp. 255–265.

Martin C. Salinsky and Kim J. Burchiel; "Vagus Nerve Stimulation Has No Effect on Awake EEG Rhythms in Humans," Epilepsia, (1993); vol. 34, No. 2, pp. 299–304.

Duncan J. MacCrimmon, Gerald J. Durocher, Roger W.Y. Chan, D. Robert Hay and Bishan M. Saxena; "Computerized Pattern Recognition of EEG Artifact," Brain Topography, (1993); vol. 6, No. 1, pp. 21–25.

Hao Qu and Jean Gotman; "Improvement in Seizure Detection Performance by Automatic Adaption to the EEG of Each Patient," Electroencephalography and Clinical Neurophysiology, (1993); vol. 86, pp. 79–87.

Gábor Jandó, Ralph M. Siegel, Zsolt Horváth and György Buzsáki; "Pattern Recognition of the Electroencephalogram by Artificial Neural Networks," Electroencephalography and Clinical Neurophysiology, (1993); vol. 86, pp. 100–109.

G.W. Harding; "An Automated Seizure Monitoring System for Patients With Indwelling Recording Electrodes," Electroencephalography and Clinical Neurophysiology; (1993), vol. 86, pp. 428–437.

J. Gotman, V. Levtova and B. Farine; "Graphic Representation of the EEG During Epileptic Seizures," Electroencephalography and Clinical Neurophysiology, (1993); vol. 87, pp. 206–214.

P.J. Allen, S.J.M. Smith, W.F.J. Harkness and D.R. Fish; "A Specialised Computer–Based Monitoring System for Intraoperative Electrocorticography," Electroencephalography and Clinical Neurophysiology, (1993); vol. 87, pp. 340–342.

Andrew F. Leuchter, Ian A. Cook, Thomas F. Newton, Jennifer Dunkin, Donald O. Walter, Susan Rosenberg–Thompson, Peter A. Lachenburg and Herbert Weiner; "Regional Differences in Brain Electrical Activity in Dementia: Use of Spectral Power and Spectral Ratio Measures," Electroencephalography and Clinical Neurophysiology, (1993); vol. 87, pp. 385–393.

J. Gotman, J.R. Ives and P. Gloor; "Frequency Content of EEG and EMG at Seizure Onset: Possibility of Removal of EMG Artefact by Digital Filtering," Electroencephalography and Clinical Neurophysiology, (1981); vol. 52, pp. 626–639.

Ronald P. Lesser, MD, Peter W. Kaplan, MBBS, FRCP; "Long–Term Monitoring With Digital Technology for Epilepsy," Journal of Child Neurology, (Oct., 1994); vol. 9, Supp. No. 1, pp. 564–570.

T. Pietilä, S. Vapaakoski, U. Nousiainen, A. Värri, H. Frey, V. Häkkinen and Y. Neuvo; "Evaluation of a Computerized System for Recognition of Epileptic Activity During Long––Term EEG Recording," Electroencephalography and Clinical Neurophysiology, (1994); vol. 90, pp. 438–443.

Jonathon R. Wolpaw and Dennis J. McFarland; "Multichannel EEG–Based Brain–Computer Communication," Electroencephalography and Clinical Neurophysiology, (1994); vol. 90, pp. 444–449.

W.R.S. Webber, Brian Litt, K. Wilson and R.P. Lesser; "Practical Detection of Epileptiform Discharges (Eds) in the EEG Using Artificial Neural Network: A Comparison of Raw and Parameterized EEG Data," Electroencephalography and Clinical Neurophysiology, (1994); vol. 91, pp. 194–204.

Steven J. Schiff, Akram Aldroubi, Michael Unser and Susumu Sato; "Fast Wavelet Transformation of EEG," Electroencephalography and Clinical Neurophysiology, (1994); vol. 91, pp. 442–455.

André Achim; "Cerebral Source Localization Paradigms: Spatiotemporal Source Modeling," Brain and Cognition, (1995); vol. 27, pp. 256–287.

Walter S. Pritchard; "Measuring "Chaos" In the Brain: A Tutorial Review of EEG Dimension Estimation," Brain and Cognition, (1995); vol. 27, pp. 353–397.

Vincent J. Samar, Kenneth P. Swartz and Mysore R. Raghuveer; "Multiresolution Analysis of Event–Related Potentials by Wavelet Decomposition," Brain and Cognition, (1995); vol. 27, pp. 398–438.

Josef Dorfmeisteer, Mark Frei, David Lerner, Ivan Osorio and John Ralston; A Comparison Between Fourier and Wavelet Transform Methods for Seizure Detection; Mar. 8, 1994.

Josef Dorfmeisteer, Mark Frei, David Lerner, Ivan Osorio and John Ralston; Method for the Prediction and Rapid Recognition of Changes of State in the Human Brain; Aug. 30, 1994.

L.M. Hiveley, N.E. Clapp, C.S. Daw, W.F. Lawkins and M.L. Eisenstadt; Nonlinear Analysis of EEG for Epileptic Seizures; Apr. 1995.

B.W. Dahanayake and A.R.M. Upton; "A Novel Approach for Epileptic Seizure Detection," 1994 IEEE Seventh Symposium on Computer–Based Medical System; Jun. 10–12, 1994; Winston–Salem, North Carolina.

Steven J. Schiff, John Milton, Joshua Heller and Steven L. Weinstein; "Wavelet Transforms and Surrogate Data for Electroencephalographic Spike and Seizure Localization," Optical Engineering, (Jul., 1994); vol. 33, No. 7.

GENERIC FIR FILTER

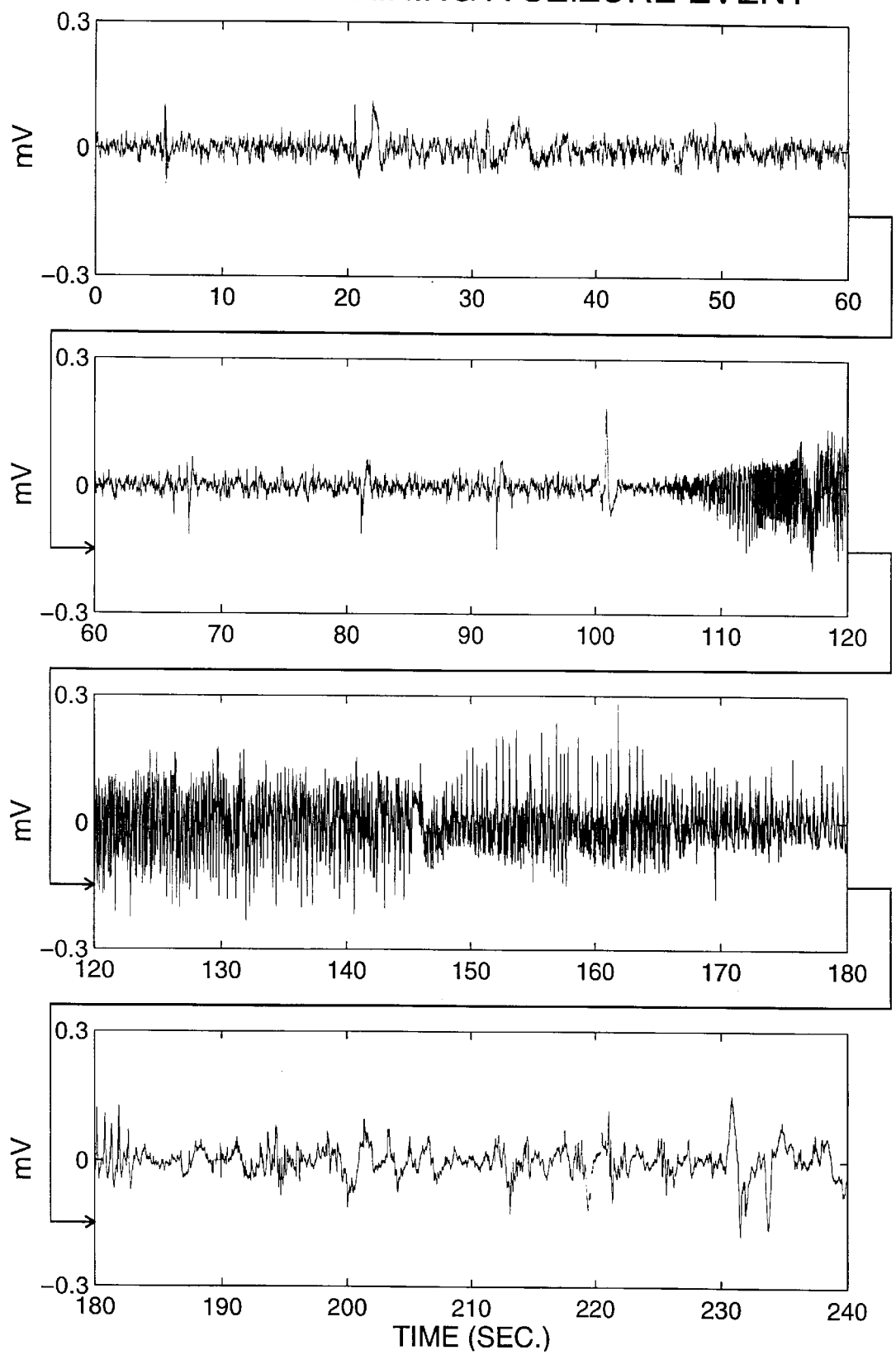
Fig. 4 ECoG CONTAINING A SEIZURE EVENT

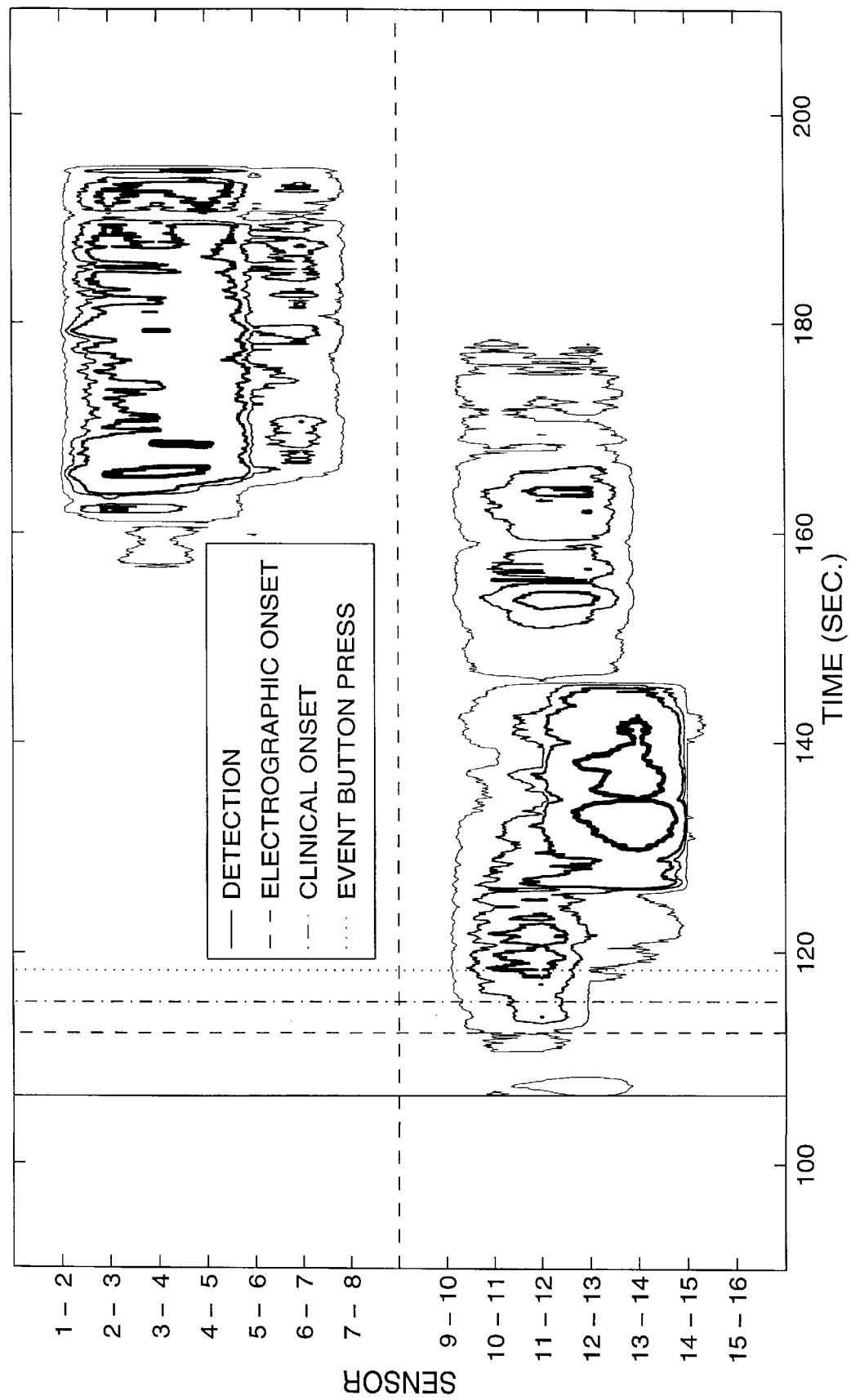

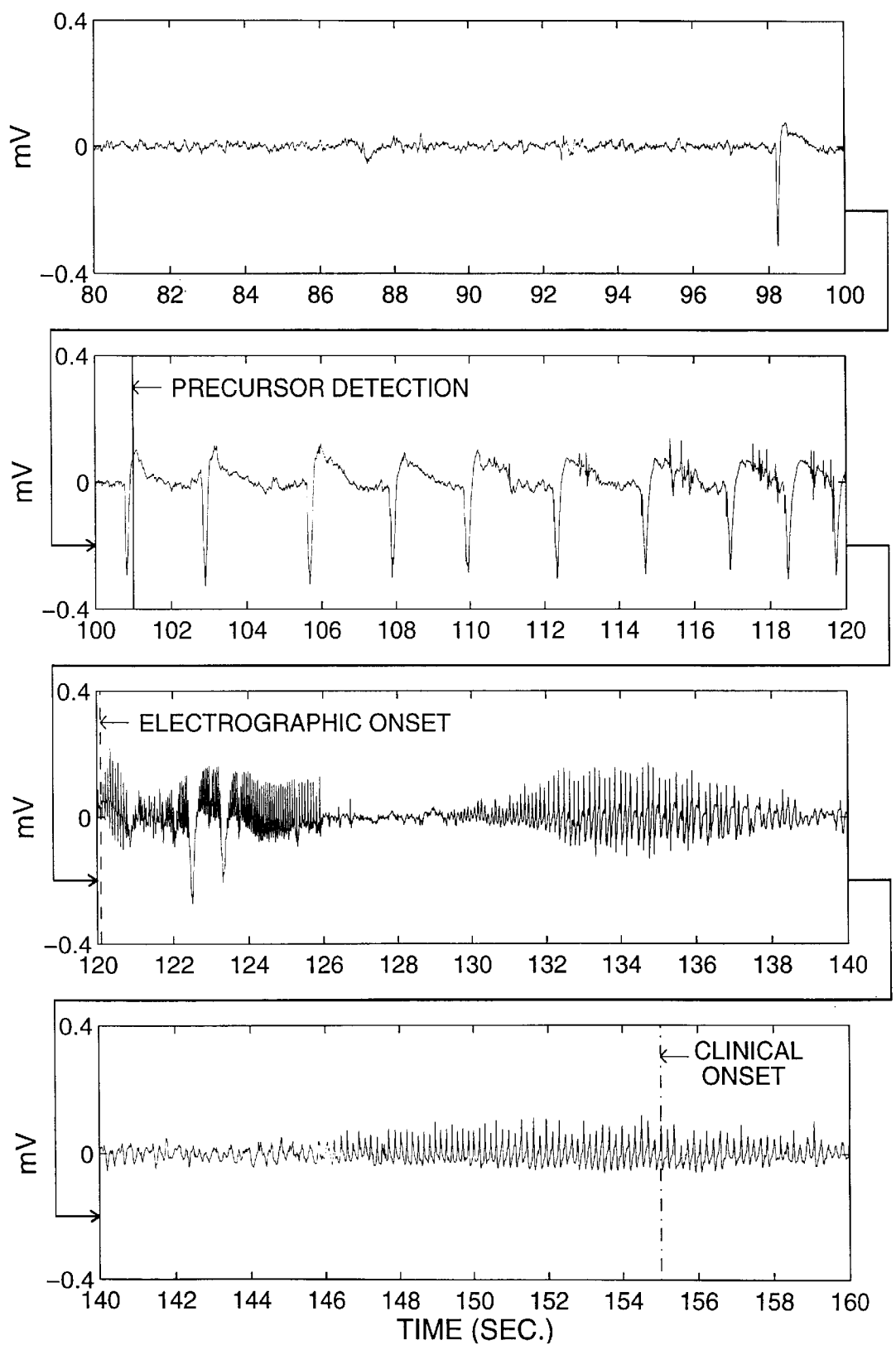
Fig. 10 ECoG DATA SHOWING A PRECURSOR

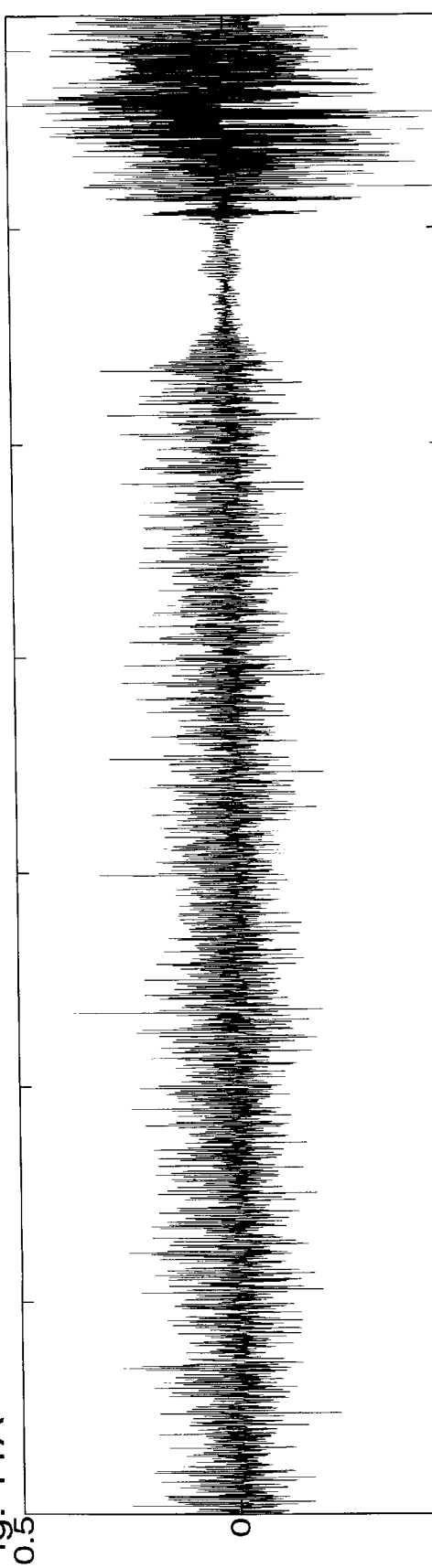
Fig. 11A ECoG SIGNAL SHOWING A PRECURSOR
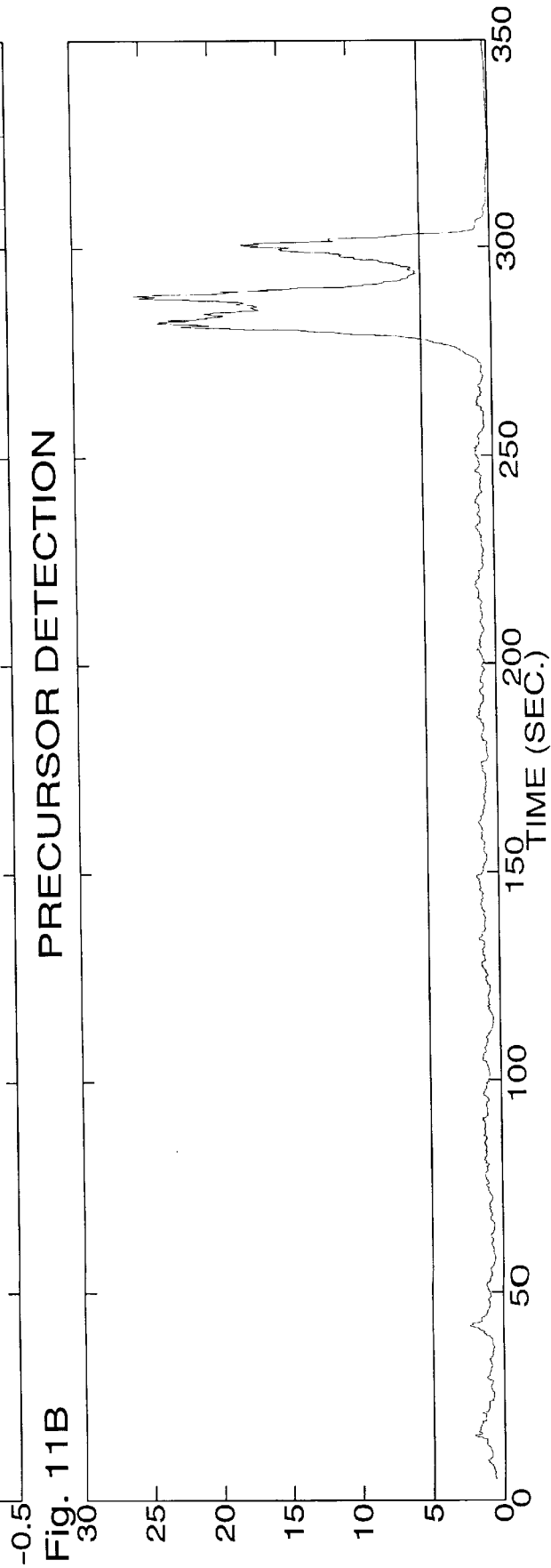
Fig. 11B PRECURSOR DETECTION

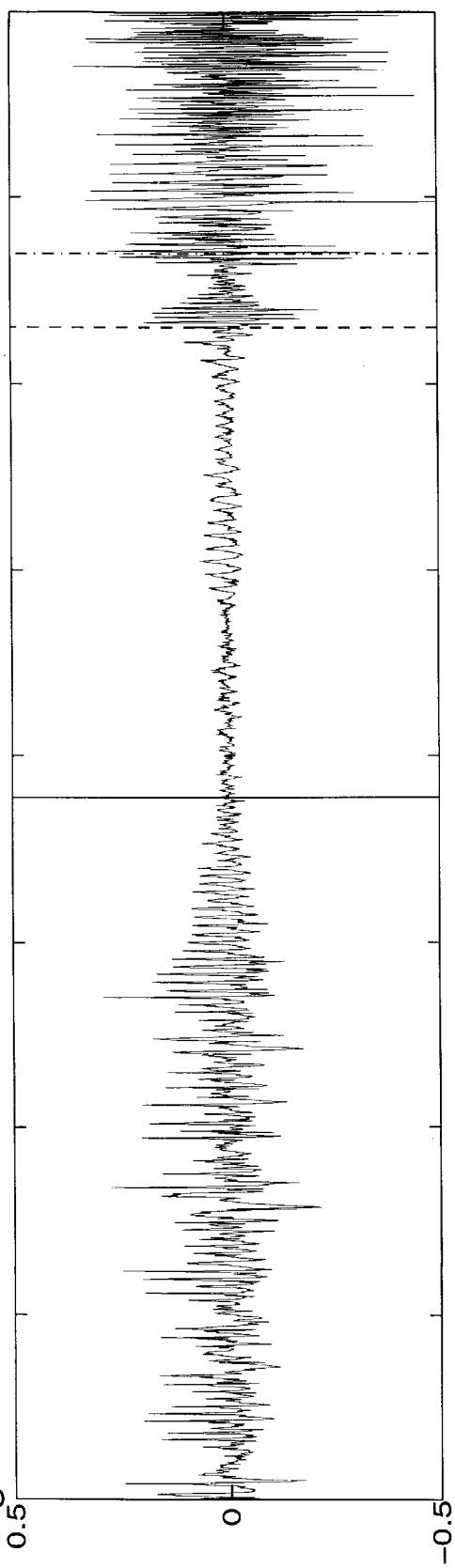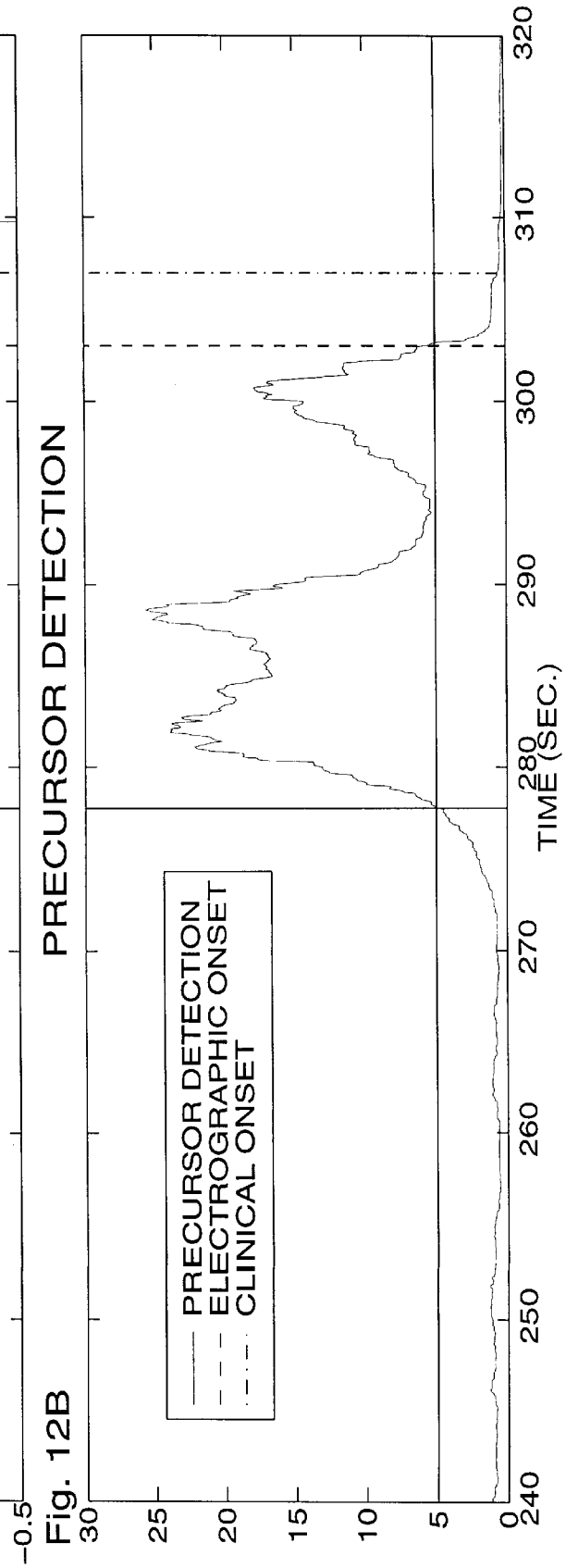

Fig. 14A  1024 POINTS OF ECoG SIGNAL
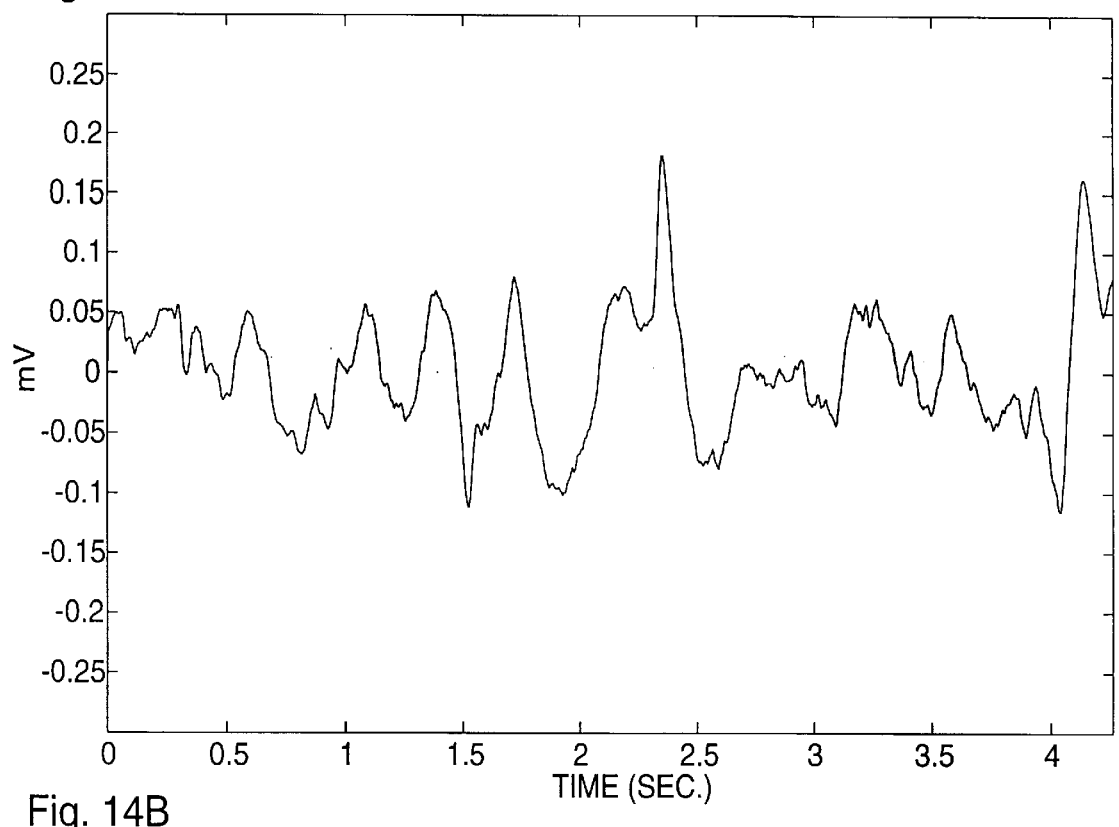
Fig. 14B
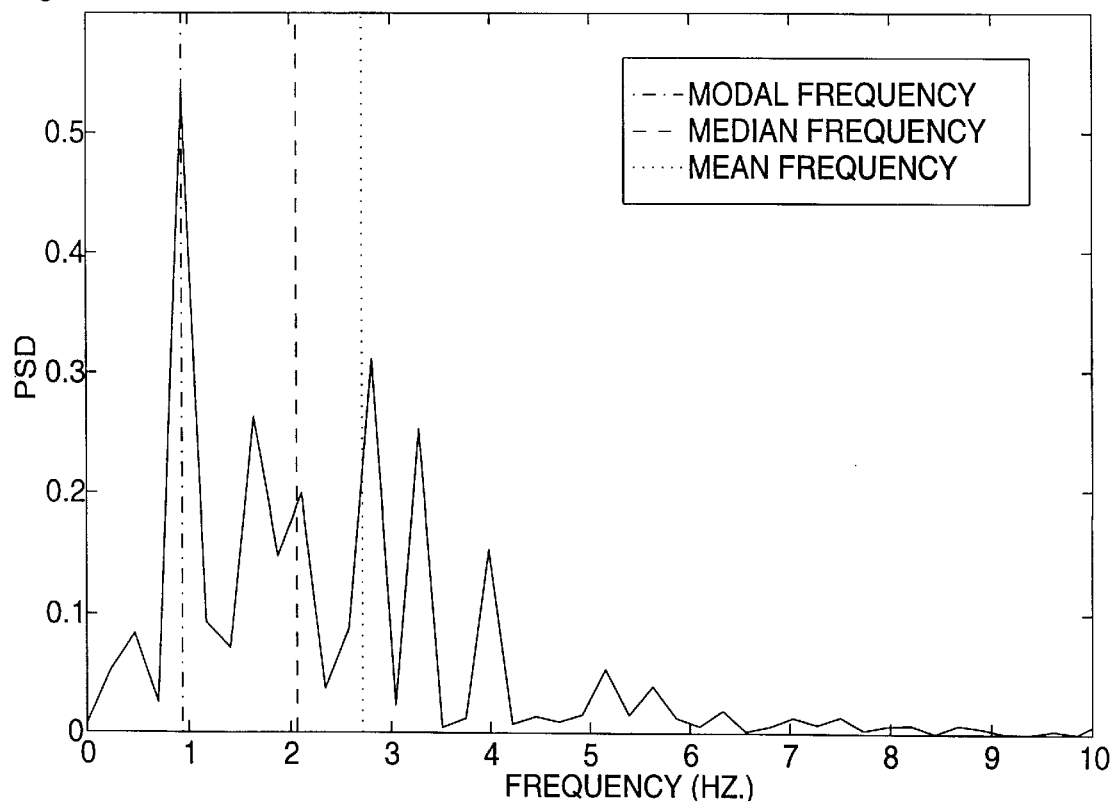

Fig. 15A    ECoG DATA

Fig. 15B    ABSOLUTE VALUE OF WAVELET COEFFICIENTS

SYSTEM FOR THE PREDICTION, RAPID DETECTION, WARNING, PREVENTION, OR CONTROL OF CHANGES IN ACTIVITY STATES IN THE BRAIN OF A SUBJECT

RELATED APPLICATIONS

This application claims priority under 35 U.S.C. § 119(e) of Provisional Application Serial No. 60/010,477, filed Jan. 23, 1996 entitled SYSTEM FOR THE PREDICTION, RAPID DETECTION, WARNING, PREVENTION, OR CONTROL OF CHANGES IN ACTIVITY STATES IN THE BRAIN OF A SUBJECT.

FEDERALLY SPONSORED RESEARCH OR DEVELOPMENT

Not applicable.

MICROFICHE APPENDIX

A microfiche appendix as Appendix 1 containing a source code of a computer program useful in accordance with the present invention is appended hereto as 1 sheet of microfiche containing 20 frames.

BACKGROUND OF THE INVENTION

1. Field of the Invention

The present invention relates to the field of neuroscience for analyzing signals representative of a subject's brain activity including signals indicative or predictive of epileptic seizures. More particularly, the invention concerns the automated analysis of brain activity signals to detect an activity state and transitions between states, and to detect precursors predictive of a change in the subject's activity state to a different state.

The invention is based on ideas and research in the fields of mathematics, neurology, statistics and engineering which enable the real-time analysis of biologic signals such as the electro-encephalogram (EEG) or electro-corticogram (ECoG), by the simultaneous execution of multiple methods. In the preferred embodiment, these signals are rapidly, accurately, and automatically analyzed in order to:

1) Detect and signal the occurrence of an epileptic seizure in real time (or contemporaneously with the arrival of the signal at the processor/device),
2) To predict behavioral changes typically associated with seizures,
3) To predict seizures by detecting precursors to the onset of the electrographic or clinical components of a seizure,
4) To detect and further analyze epileptiform discharges (spikes), and
5) To download the detection or prediction outputs to devices for warning, or therapeutic interventions or the storage of data.

2. Description of the Prior Art

Humans and animals have several normal states of behavior such as wakefulness and sleep, as well as multiple sub-states such as attentive wakefulness and REM sleep. Abnormal states include reversible states such as seizures and progressive states such as dementia.

Epilepsy, a disabling disease, affects 1–2% of the American and industrialized world's population, and up to 10% of people in under-developed countries. Electroencephalography is the single most important ancillary test in the investigation of this disease. EEG's are recorded continuously for hours to days in an increasing number of cases with unclear diagnosis or poor response to adequate medical treatment. The amount of EEG data for analysis is extremely large (e.g., 64 channels of data at 240 Hz gives 1.3 billion data points/24 hr or 2.6 Gigabytes/day) and consists of complex waveforms with infinite variations.

Visual analysis of these signals remains (exclusive of this invention) the "gold standard" but it is impracticable for continuous EEG interpretation as this is the most time-consuming part of any electrodiagnostic test and requires special training and skills which make this procedure expensive and thus of limited access and use. Valuable EEG data is often discarded unexamined. The length of recording is unnecessarily prolonged in a specially equipped hospital suite until patients have several seizures. If the patient is unaware of the seizures, a common occurrence, then a nurse or relative must observe and document the occurrence of these changes. As seizures are brief and previously considered unpredictable, the need for continuous observation becomes imperative, adding to the cost in a non-effective manner.

Present methods of seizure detection are not only expensive, but rely on poorly discriminating methods, increasing the review time and nursing assistance because of the large number of false positives, and increasing the length of hospitalization through the false negatives. Furthermore, these methods often "detect" the seizure well after its onset or even its end, when prevention or abatement of the seizure is not possible or irrelevant.

The inability to process data in real time has thwarted the scientific and clinical development of the fields of epilepsy and electroencephalography. Cardiology has developed into a clinical science largely based on the power of electrocardiography to analyze the heart's electrical activity in a rapid and accurate manner. This has resulted in pacemakers, implanted defibrillators, and other devices which have saved thousands of individuals from premature death. The comparison between cardiology/EKG and epilepsy/EEG must take into account the fact that the electrical brain signals are far more complex than those originating from the heart. This explains in large part the developmental lag between these two disciplines.

Electrical brain signals, because of their spatial and temporal characteristics such as non-stationarity, have resisted accurate real-time automatic manipulation. The prior art methods presently used to characterize these states are severely limited. For example, the prior art consists of a long history of failed attempts to identify changes in EEG during certain behavioral states or tasks and to discern epiphenomenology from phenomenology, a distinction that would help answer questions of fundamental importance. Other limitations include the inability to determine whether spikes are a static marker of epilepsy, or whether they are dynamically related to seizure generation.

Present methods of automatic EEG analysis have many major limitations which render them virtually useless for widespread, safe and effective clinical applications. These limitations include:

1) Lack of speed. The time it takes most methods to analyze the input signals and produce an output which detects or predicts a state change is too great for use in warning, intervention, or prevention of epileptic seizures and other abnormal brain states.
2) Lack of accuracy. Prior art methods have a large number of false positives (incorrectly identifying non-seizure activity as a seizure) and false negatives (failure to identify a true seizure), increasing the technical and financial burden.

3) Lack of adaptability to subject or seizure type; no compromise between speed vs. accuracy.
4) Lack of portability and implantability.
5) High cost.

Accurate and reproducible prediction of behavioral or biologic signal changes associated with seizures has not been possible as these events occur unpredictably. Our methods and devices enable seizure prediction by providing a worthwhile prediction time that makes warning, abortion/abatement, and prevention of seizures possible. The new treatment modalities that can be based on this method will lead to a significant reduction in seizure frequency and, consequently, to a reduction in the occurrence of injuries and fatalities, allowing persons with epilepsy to become productive and lead normal lives.

The prior art in automated seizure and spike detection consists of variations of two primary methods: "rule-based" analysis and, more recently, analysis by artificial neural networks. The most popular is a "rule-based" method which has been under development since the late 1970's, primarily by Dr. Jean Gotman. In the Gotman method, the signal is initially replaced by a piecewise linear approximation which connects maxima and minima.

In the Gotman method, there is a list of rules which are then applied to throw out some of the smaller line segments in an attempt to remove fast activity that is superimposed on an underlying wave of interest. The larger line segments which remain are called "half waves." Gotman's algorithm then compares properties of the half waves such as averages of amplitude, duration, rhythmicity, and sharpness in moving ⅓ sec. windows to those of past and future data segments. As currently implemented, the method uses a total of 30 seconds of past data and 8–10 seconds of future data in these comparisons. A set of rules and thresholds are given to determine when these comparisons of past, present, and future properties yield a detection of a spike or seizure.

These rule-based methods have a number of limitations, including a large false positive rate, and usually a long delay to detect even abrupt changes (often 10 or more seconds).

Another method for spike and seizure detection involves training an artificial neural network (ANN) using past data tracings with annotated spikes and seizures to "learn" to recognize similar changes in unseen data. The large number of "neurons" required for accurate analysis of a multichannel EEG/ECoG input signal precludes real-time analysis. Consequently, the current state of the art implementations rely on a smaller number of "neurons" and a parametrized input signal in place of the raw signal. The Gotman half-wave decomposition mentioned above is commonly used in this signal parametrization step—causing the inclusion of many of the limitations inherent in this method to adversely affect the ANN methods. In addition, the adaptation of an ANN to improve its performance for a particular individual or group is performed off-line and requires time consuming retraining by experienced epileptologists. This important limitation is overcome by the present invention.

3. Glossary of Terms and Useful Definitions

The onset of the clinical component of a seizure is the earlier of either (1) the time at which the subject is aware that a seizure is beginning (the "aura"), or (2) the time at which an observer recognizes a significant physical or behavioral change typical of a seizure.

The onset of the electrographic component of a seizure is defined by the appearance of a class of signal changes recognized by electroencephalographers as characteristic of a seizure. This analysis requires visual review of signal tracings of varying duration, both before and after the perceived signal changes, using multiple channels of information and clinical correlates. The precise determination of the onset is subject to personal interpretation, and may vary based on the skill and attention level of the reviewer, the quality of data and its display.

The electroencephalogram, or EEG, refers to voltage potentials recorded from the scalp. EEG will encompass any recordings outside the dura mater. The electrocorticogram, or ECoG, refers to voltage potentials recorded intracranially, e.g., directly from the cortex. EKG is the abbreviation for electrocardiogram, EMG for electromyogram (electrical muscle activity), and EOG for electrooculogram (eye movements).

The period of time during which a seizure is occurring is called the ictal period. (Those skilled in the art will appreciate that the term ictal can be applied to phenomena other than seizures.) The period of time when the patient is not in the state of seizure, or in transition into or out of the seizure state, is known as the interictal period. The preictal period corresponds to the time of transition between the interictal and the beginning of the ictal period, and the postictal period corresponds to the time period between the end of the seizure and the beginning of the interictal period.

Herein the term real-time describes a system with negligible latency between input and output.

The term false positive refers to the case of a system mistakenly detecting a non-seizure signal and classifying it as a seizure. The term false negative describes the case in which a true seizure goes undetected by a system. Systems that have a low rate of false positive detections are called specific, while those with a low rate of false negative detections are called sensitive.

The terms epileptiform discharge and spike are used interchangeably herein to refer to a class of sharply contoured waveforms, usually of relatively large power, and with duration rarely exceeding 200 msec. These spikes can form complexes with slow waves, and can occur in singlets or in multiplets.

The terms epileptologist and electroencephalographer are used interchangeably.

SUMMARY OF THE INVENTION

The present invention solves the problems and overcomes the limitations of prior art, while providing pioneering advances in the state of the art. Its preferred embodiment enables (1) the accurate, automated, real-time detection of seizures, as well as the determination of their site of origin, propagation path and speed through regions of the brain, and their duration and intensity; (2) the prediction of the onset of the clinical component of seizures; (3) the prediction of the onset of the electrographic component of seizures; (4) the online self-adaptation, or offline adaptation of (1–3) to each individual, (5) the automated use of (1–3) for diagnosis, quantitative analysis, imaging, warning, treatment, and storing of data; and (6) the miniaturization of the system to a portable or implantable device.

The adaptation of the system to each individual takes into account, seizure type and location, and changes in the signal(s) over time, making use of any existing preictal, ictal, or postictal "fingerprints" for the subject. The speed of analysis and levels of sensitivity and specificity can also be adjusted to desired levels, and the method can be implemented in either digital or analog form (or a combination).

The preferred embodiment of the invention uses intracranial or scalp electrodes to obtain signals representative of current brain activity and a signal processor such as a personal computer or micro-processor, for continuous monitoring and analysis of these signals, detecting important changes or the appearance of precursors predictive of an impending change, as soon as they occur. The output of this analysis is then fed to a device which produces an immediate response (e.g., warning, treatment or storage) to the change or predicted change in state. The signal processing includes an adaptive analysis of frequency, energy, wave shape and dynamics, phase relationships, measures of rhythmicity, "sequency," and temporo-spatial stereotypia, variability, dimension, complexity of the signal, and noise reduction.

1. Methods for Real-Time Seizure Detection

The following is an overview of the steps which comprise the preferred embodiment of the invention for real-time seizure detection.

(1) Extract from the entire signal the part with ictal characteristics. This step is accomplished with adaptive filtering, allowing the selection of patient- and/or sensor-specific initial parameters, and an adaptation process in which these filters automatically improve as important signal characteristics are learned online.

(2) The output of this filter is used to compute an index of ictal activity in each current signal epoch (the "foreground"), which is then divided by a corresponding measure associated with the background signal, forming a ratio. Novel application of median filtering and time and state weighted averaging are used in this step.

(3) When the value of this ratio reaches a particular threshold level, a seizure detection is immediately signaled.

(4) Grading and verification of seizures is then accomplished using an analysis of duration, intensity, pattern recognition of spatio-temporal propagation, and postictal seizure signal changes.

In addition, a new seizure imaging method has been developed based on the detection methodology presented here.

2. Methods for Detecting Precursors to Seizure

These embodiments detect the occurrence of signal characteristics or patterns which may be precursors to the clinical and/or electrographic components of seizure, resulting in their prediction. Determination of the onset of a seizure by visual analysis (which is considered "the gold standard") is a subjective and empiric process, at the present level of scientific development. Determination of time of seizure onset depends in part upon the specifications and parameters associated with the recording devices and of the location and type of sensors in reference to the tissue from where the seizure originates. The intensity and degree of spread of the seizure also affects detection.

From a practical standpoint, prediction based on the detection of seizure precursors or the electrographic component itself yield a worthwhile time during which warning and intervention can be instituted to abort or prevent the onset of either of the components of the seizure. By virtue of their self-tuning ability (detailed in a later section), the continued application of these prediction methods to a given individual or seizure type may improve the reliability of subsequent predictions, and may lengthen the predictively worthwhile time.

Seizure precursors include, but are not limited to:

(1) certain significant patterns of epileptiform discharges (or spikes), (2) significant abrupt attenuation of signal energy on some or all sensors, and (3) significant changes in various characteristics of the power spectral density associated with each of the signals that are being monitored, e.g., a sudden significant drop in the median frequency of a given signal.

Prediction of seizures may occur during different stages of their temporal evolution:

a) Prediction of the vibratory (or first) state, i.e., the state before the seizure spreads beyond the anatomical or functional boundaries of the "critical epileptogenic mass" (defined as the smallest mass that, once fully synchronized, consistently generates the next states).

b) Prediction of the electrographic component of seizure. This component is mainly defined by temporal continuity of the ictal signal with or without evolution across a frequency spectrum and with some degree of propagation outside the critical mass. Prediction of this state can be made by identifying precursors (see examples). Precursors have temporal, spectral, and other characteristics which distinguish them from the electrographic component.

c) Prediction of the clinical component of seizure. The real-time detection of the electrographic seizure component is akin, for partial or secondarily generalized seizures to the prediction of the clinical onset as there is a latency between the two components. Precursor detections further lengthen the predictive time of the clinical component.

3. A Method for Spike Detection, Classification, and Counting

The invention also includes a new method for measuring signal "sharpness," which we refer to as least-squares acceleration filtering (LSA-filtering), that is used as the basis for a new spike detection method. It can also be used to improve existing spike detection methods. In this method, the signal is continuously monitored for the occurrence of such things as spikes, and their amplitude, frequency, waveform, "sequency" (degree or pattern of clustering), rate of occurrence, location, and polarity, are computed and stored. This information is then analyzed for conformance to any seizure precursor pattern.

4. Devices for the Detection of Seizures, Precursors, and Spikes, and for the Prediction of Seizures The algorithms listed above and defined in detail herein can be realized in digital or analog form in a signal processor. The preferred embodiment has been implemented in an Intel 486 based PC for real-time monitoring and storage of data for patients undergoing clinical evaluation.

The real-time detection of:

(a) seizure precursors and the resulting prediction of the electrographic and clinical seizure components, (b) the electrographic component and the resulting prediction of the clinical component, or (c) spikes, enables the institution of safety and therapeutic measures, and initiates or continues the adaptation and self-learning of the methods. For example, a seizure prediction can be used to trigger a device for systemic, intraventricular, or intracerebral administration of a medicament or substance, for electrical, magnetic, or thermal activation or deactivation of a nerve or a region of the subject's brain, for activation or deactivation of physiologic receptors, for ablation of a region of the subject's brain, for activation of a warning or biofeedback device, or for selection of segments of signals for transmission or storage (or for annotation of continuously recorded signals) and further off-line analysis.

BRIEF DESCRIPTION OF THE DRAWING FIGURES

FIG. 4 is a graphical illustration of an ECoG signal used as an input to the apparatus of FIG. 1;

FIG. 7 is a graphical illustration of an embodiment for a seizure imaging method and apparatus applied to 16 simultaneous ECoG recordings containing a seizure event;

FIG. 10 is a graphical illustration of an ECoG signal which contains a seizure precursor signal (the quasi-periodic epileptiform discharge precursor detailed in Example 1). In this Figure, the times of the electrographic onset of the seizure, the clinical onset of the seizure, and the time of detection of the seizure precursor using an embodiment of the invention are annotated;

FIG. 11A is a graphical illustration of an ECoG signal of a subject which contains a seizure precursor signal (the signal attenuation precursor detailed in Example 2);

FIG. 11B is a graphical illustration of the output of the precursor detection embodiment for this type of seizure precursor;

FIG. 12A shows the illustration of FIG. 11A with the time axis restricted to a smaller range of times which still include the detection time of the seizure precursor, and the times of the electrographic and clinical onsets for the seizure;

FIG. 12B shows the illustration of FIG. 11B with the time axis restricted to a smaller range of times which still include the detection time of the seizure precursor, and the times of the electrographic and clinical onsets for the seizure;

FIG. 14A is a graphical illustration of 4.27 sec. of ECoG signal data.

FIG. 14B is a graphical illustration of the power spectral density (PSD) of the signal in FIG. 14A, showing the modal frequency, median frequency, and mean frequency of the signal;

FIG. 15A is a graphical illustration of 2 seconds of ECoG signal recorded from a subject during an interictal (non-seizure) period; and FIG. 15B is a graphical illustration of the absolute value of wavelet coefficients from levels 1–4 obtained by applying the fast wavelet transform to the signal of FIG. 14A.

DETAILED DESCRIPTION OF THE PREFERRED EMBODIMENTS

Figure 1:
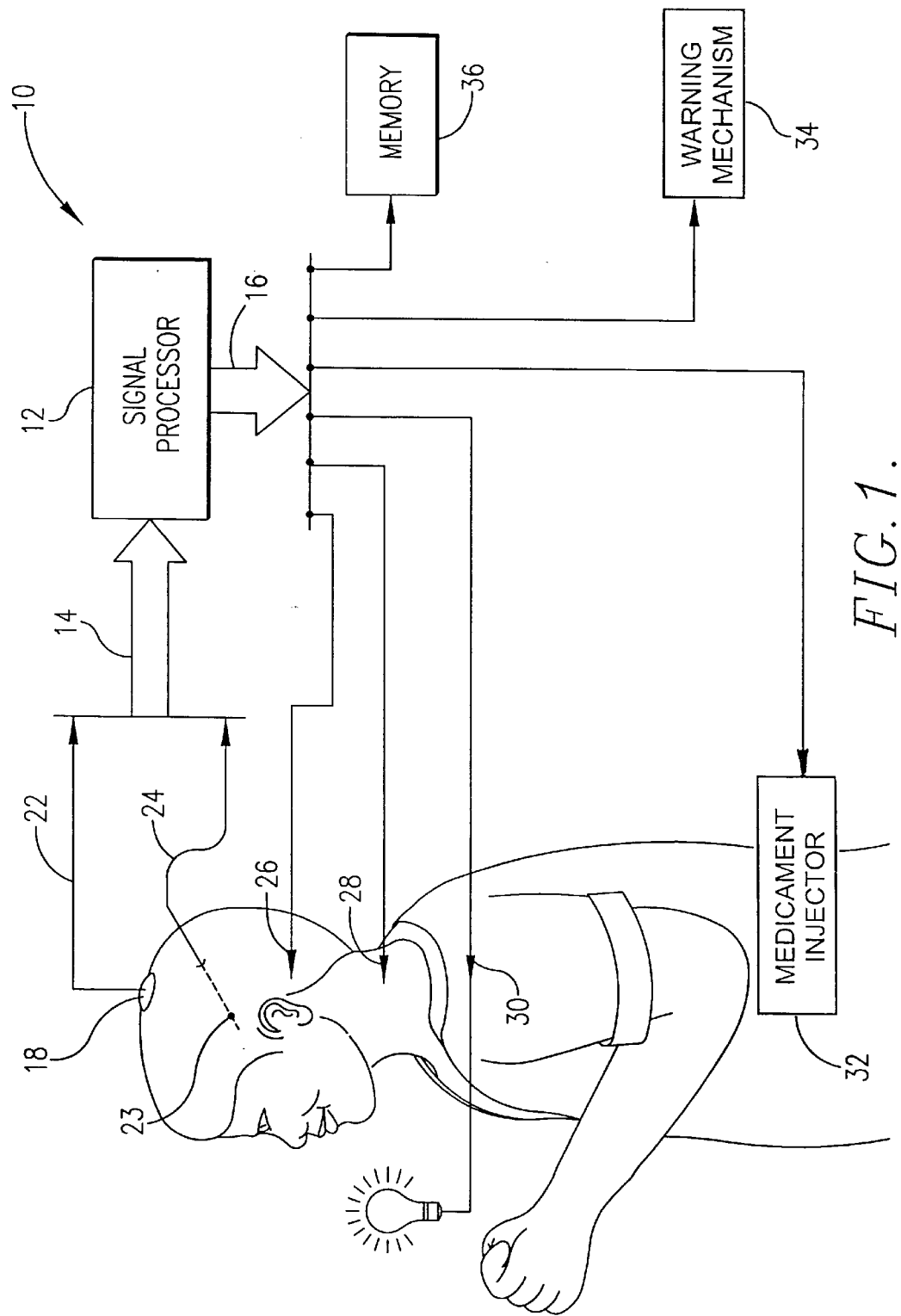
FIG. 1 is a schematic illustration of the preferred apparatus of the present invention showing inputs of brain (or other biologic system) signals of a subject from surface and/or implanted (e.g., intracranial) sensors to a signal processor and various types of outputs.
Figure 2:
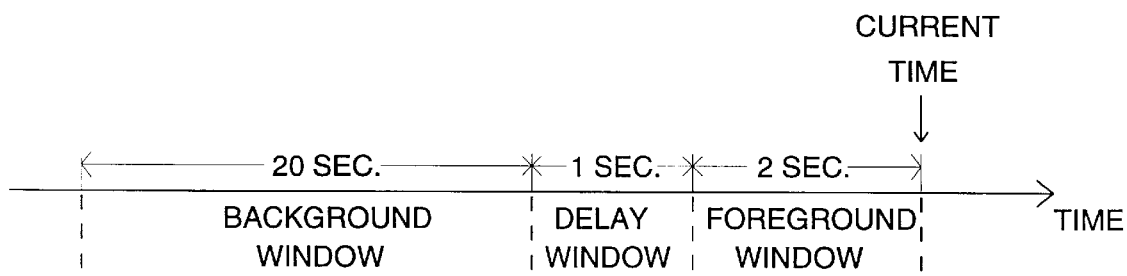
FIG. 2 is a graphical illustration of the segments of data which may be used in one preferred seizure detection method for operating the apparatus of FIG. 1 to represent current ("foreground") signal activity (e.g., the most recent 2 seconds), and signal background activity (e.g., a segment of 20 or more seconds in length) delayed 1 second from the end of the foreground window.

FIG. 1 illustrates the preferred apparatus 10 for receiving and analyzing signals representative of a subject's brain activity and for producing different types of outputs. Apparatus 10 includes signal processor 12, inputs 14 and outputs 16. Signal processor 12 is preferably a computer such as one with capabilities that meet or exceed those of an Intel 486-based computer having 33 MHz clockspeed and 8 MB of RAM. Those skilled in the art will appreciate that an appropriate digital signal processor can be used in place of the preferred computer, as could a custom-designed semiconductor chip having the requisite capability, preferably configured for implantation or as a portable device. Signal processor 12 could also be an analog processor or an analog/digital combination. Appendix 1 is incorporated as part of the disclosure hereof and contains the presently preferred computer program for use by apparatus 10 and, in particular, signal processor 12, and for implementing the preferred methods of the present invention as further described herein.

Inputs 14 include EEG (or other type of scalp) signals obtained from a plurality of scalp sensors 18 transmitted through associated lines 22, or ECoG signals obtained from implanted sensors 23 and transmitted through associated lines 24. The input signals used in the development of this invention were amplified and converted from analog to digital form at a rate of 240 Hz with a dynamic range of [−300,300] $\mu V$ and digital resolution of 0.59 $\mu V$ (10 bits of precision per datum). This provides 144 Kb of data per minute, per channel. Those skilled in the art will appreciate that sampling may be performed at fixed or varying rates (higher or lower than 240 Hz) and precision (with more or less precision than 10 bits), using linear or nonlinear analog to digital conversion, and with constant or varying dynamic range (i.e., adjustable gain). Data acquisition may also be performed using adaptive sampling techniques, in which these sampling parameters vary over time and are determined by characteristics of the signal being sampled. Adaptive sampling techniques can be used to selectively enhance relevant signal characteristics and increase signal quality and resolution in certain frequency bands.

Outputs 16 can trigger portable or implanted devices, electrodes 26 which may be intracranial or extracranial, or placed over or around a nerve 28, a medicament injector or pump 32, an audio or LED output or any other form of warning 34, and auxiliary memory 36 for storing input signals and event data. Implanted electrodes 26 can be used for any form of activation or deactivation (e.g., electrical, thermal, etc.) of local or remote brain cells or for ablation of the epileptogenic tissue. Nerve stimulator 28 is preferably associated with the vagus nerve as such stimulation has been found to abate or prevent a seizure. Physiologic (or natural) stimulation to receptors (e.g., light to retinal receptors) can prevent or abate seizures and is the function of stimulator 30. Injector 32 is preferably implanted for automated instantaneous release of the appropriate medicament (inclusive of any efficacious substance) for treating, preventing or abating a seizure. Memory 36 is provided to store signal and event data for archival and analysis purposes.

As discussed further herein, the analysis performed in signal processor 12 can be customized for a particular patient to improve the detection of brain states and state transitions, and the prediction of changes in brain states. The customization of the signal processing can be based on the information stored in memory 36 via feedback of this information to signal processor 12. For example, this information may be used to monitor efficacy of treatment and to optimize seizure/spike detection and prediction, and therapeutic or safety interventions. Those skilled in the art will also appreciate that memory 36 can be included as an integral part of signal processor 12.

Those skilled in the art will recognize that changes in cerebral state are highly correlated with changes in level and type of activity of other organ systems (e.g., heart, etc.) and as such these signals, may be useful for detection and prediction or validation of seizures or of other changes in brain state. The following signals (not annotated in FIG. 1) may be used in conjunction with EEG and ECoG signals to further improve performance of the system:

1) Non-electrical cerebral (global or regional) signals, such as concentrations of glucose, free radicals, metabolic by-products, neuro-transmitters, or other substances, or measurements of intracranial pressure, temperature, blood flow or indices of metabolic activity, etc.,
2) Cardiovascular signals such as heart rate, R-R interval and variability, etc.,
3) Respiratory signals such as tidal volume, peak-to-peak interval, etc.,
4) Electrodermal and other DC potentials,
5) Signals representative of concentrations in the blood or other peripheral tissues of gases, substances, or chemicals such as lactic acid, etc.,
6) Signals representative of the level or type of activity of cranial or peripheral nerves (e.g. frequency and pattern of action potentials, etc.),
7) Signals related to EMG activity, force, direction, and patterns of limb or body movements.

Real Time Seizure Detection

Successful real-time detection of seizures depends on the ability of any method to rapidly and accurately distinguish the ictal from the non-ictal part of the signal. We begin with a detailed description of the generic method, then discuss additional features and modifications which are used to enhance its sensitivity and specificity by making it adaptive, i.e., allowing it to learn online. The preferred embodiment as detailed here is based on a sampling rate of 240 Hz with 10 bits of precision. However, there is a wide range of digitization techniques which may be used, together with the appropriate modifications to the algorithm's parameters. FIG. 4 shows a 4 minute segment of ECoG signal which is used to illustrate a preferred embodiment for detecting the electrographic component of a seizure.

Figure 3A:
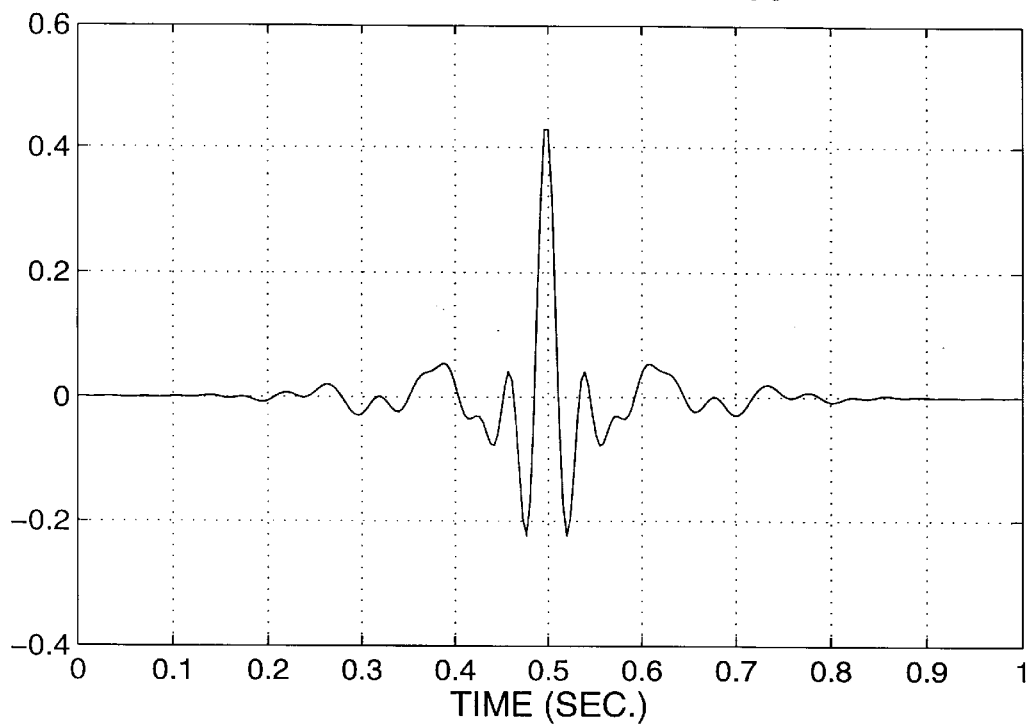
FIG. 3A is a graphical illustration showing a finite impulse response (FIR) filter which may be used in the first step of the preferred embodiment for detecting seizures in the input signals to the apparatus of FIG. 1.
Figure 3B:
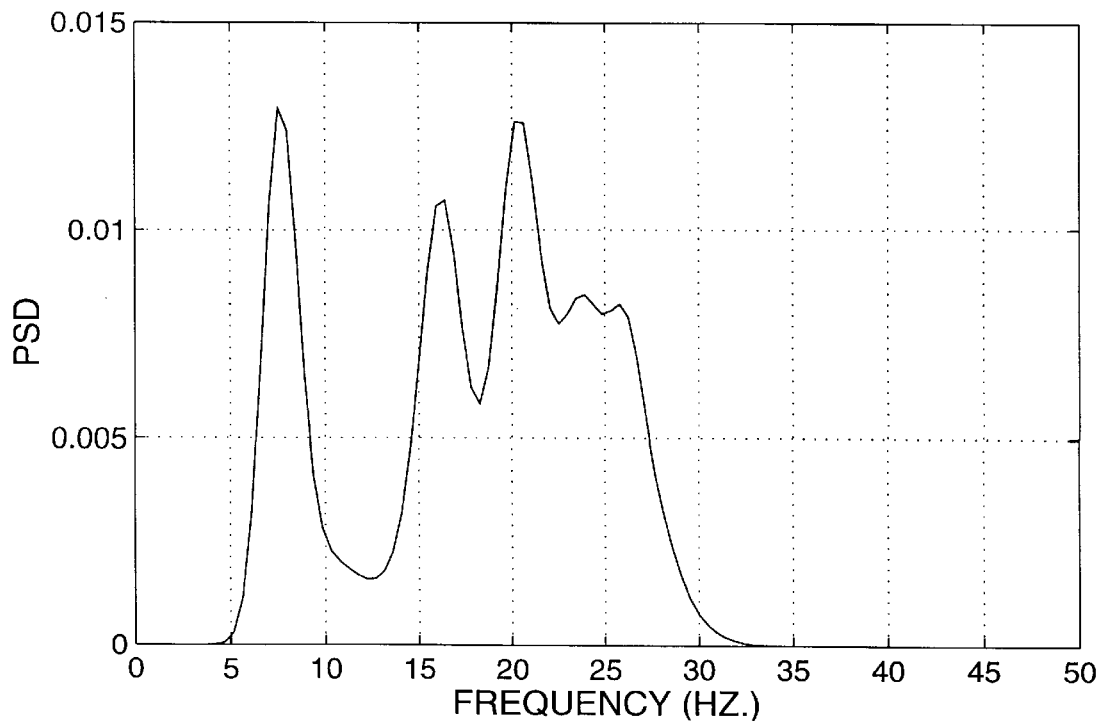
FIG. 3B is a graphical illustration showing the power spectral density (PSD) associated with the FIR filter of FIG. 3A.

The first step of the method consists of applying a filter to the signal to decompose the entire signal into its ictal and non-ictal components. As a result of research performed for this invention, identification of key differences between ictal and non-ictal signal characteristics was successfully accomplished. These results enabled the construction of filters to accomplish this first step of the method. These include "generic" digital filters of both finite impulse response (FIR) (also known as a convolution filter and moving average (MA) filter) or infinite impulse response (IIR). One such FIR filter is shown in FIG. 3, together with an estimate of its power spectral density (PSD). These filters could include analog filters as well and were constructed using a data base of over 100 seizures in the following manner:

1) Each seizure was divided into segments according to its temporal evolution, and the PSD of each segment was computed;
2) The resulting PSD's were then compared with PSD's obtained from interictal segments. Power-frequency envelopes were then computed, more heavily weighing the spectra at frequencies which yielded the greatest separation between the ictal and interictal PSD values.
3) The orders and type (e.g. FIR or IIR) of the "generic" filters were then chosen, taking into account the trade off between computational burden/speed and goodness-of-fit of their impulse response to the desired shape. The filter coefficients were then computed from the desired impulse response using standard filter design methodology.

Those skilled in the art are aware of the many degrees of freedom or options available in designing filters. For instance, the magnitude and phase specifications of the filter's impulse response may be adjusted to match the PSD characteristics of a set of seizures, or infinite impulse response (instead of FIR) filters may be used when speed of processing is the primary objective, especially if the filter must precisely discriminate between extremely low frequencies (e.g., less than 2 Hz.). Genetic algorithms provide a useful approach to solving the multi-dimensional constrained optimization problem of designing a best filter for a given set of data.

For a given subject, a filter is initially selected from the filter bank. This selection can be done off-line by a clinician upon a study of archival wave forms. In the alternative, the selection can be completed on-line by applying all the filters in the filter bank individually to the input signals and selecting that filter that produces the greatest differentiation.

If the input signal is given by $\{x_j\}_{j=1}^n$, and the FIR filter has m coefficients $\{b_0, b_1, \ldots, b_{m-1}\}$, then the output (filtered) signal $\{Y_j\}_{j=1}^n$ is obtained from the formula $$Y_{k+1} = b_0 x_k + b_1 x_{k-1} + b_2 x_{k-2} + \ldots + b_{m-1} x_{k-m+1},$$

where it is assumed that $x_j=0$ for all $j<1$.

Figure 5A:
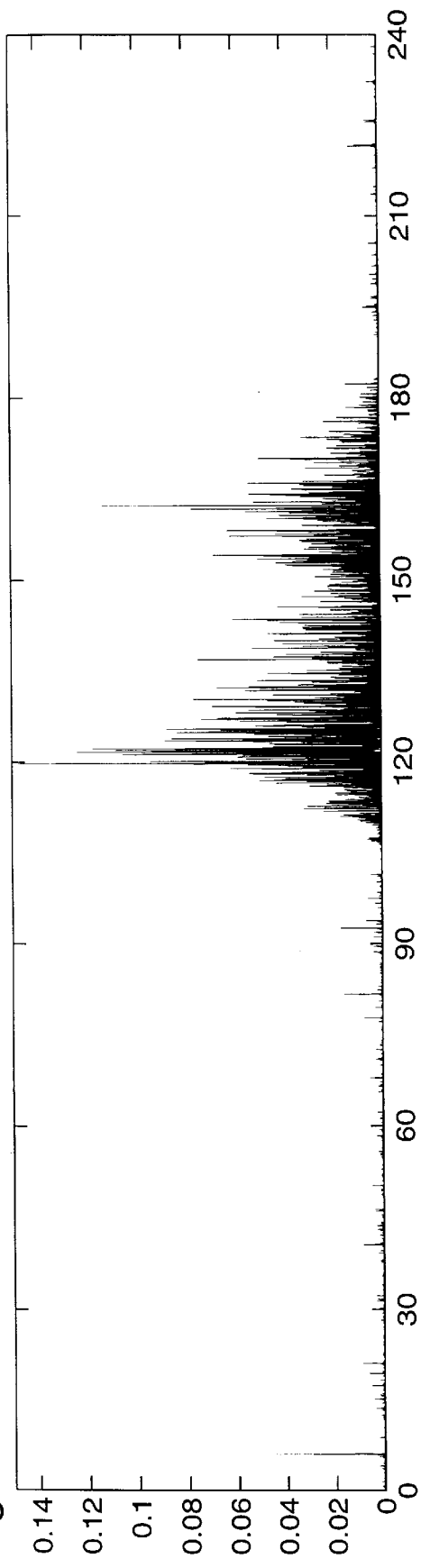
FIG. 5A is a graphical illustration of the result of applying the generic FIR filter of FIG. 3A to the signal of FIG. 4, and squaring the output signal values in an embodiment of the invention.

The output of this filter is then squared, and the evolution of the resulting $Y_k^2$ values is monitored, comparing the most recent values (the "foreground") to less recent values (the "background"), to detect relevant changes. FIG. 5A shows the graph of the $Y_k^2$ values which result from the application of the FIR filter described above to the signal of FIG. 4, and then squaring the output.

In the next step of the method, we shall refer to the present information as "foreground," and compare it to the signal history or "background." Once the raw signal has been filtered to extract and enhance its ictal part, the next step in the method is to use the $\{Y_k^2\}$ sequence to create measures of the level of ictal activity in the most recent signal epoch, and compare it with that contained in the interictal signal. To compute a measure of ictal activity in the foreground, we apply a (nonlinear) median filter of order 480 (2 seconds) to the $\{Y_k^2\}$ sequence, to obtain the sequence $\{F_k\}$ (240 values per second per channel), $$F_k = \text{median}\{Y_{k-p+1}^2, Y_{k-p+2}^2, \ldots, Y_{k-1}^2, Y_k^2\},$$

where p is the order of the median filter (e.g., p=480 @ 240 Hz.). This step is used to monitor a change in central tendency of the distribution of the recent (foreground) $Y_k^2$ values. The median (or other order-statistic is preferred for this step because of its ability to measure the central tendency of a distribution without being overly sensitive to outliers such as those which result from single or multiple spikes.

To compute a measure of the ictal activity in the background, $\{B_k\}$, which is used as a reference against which foreground changes are measured, we apply another median filter to the $Y_k^2$ values, with the following modifications:

1. The order is increased (e.g., to 20 seconds, p=4800) to obtain a more stable background,
2. The filter is delayed by a certain time (e.g., 1 second) from the current time to remove any possible effect of the most recent signal on the background value, $B_k$, thus making a foreground change easier and faster to distinguish/detect,
3. Updates of background, $B_k$, are disabled during seizures or other anomalies (e.g., transient artifacts), and
4. An exponentially forgetting time average (or a more general time- and state-weighted average) of this delayed median filter output is used to increase the period of signal history represented by the background sequence, $\{B_k\}$, without increasing memory/storage requirements or computations. Use of this technique decreases the size and number of fluctuations in this background sequence, improving detection by allowing more sensitive thresholds to be set without significantly increasing false detections. Details regarding more general time- and state-weighted averaging techniques which may be employed in this step are presented in Appendix 2 which is incorporated as part of the disclosure hereof.

To now be more precise, the background sequence, $\{B_k\}$, is computed as follows. We begin by applying a delayed median filter of order h and delay d to the squared output of the FIR-filter, $\{Y_k^2\}$, to obtain the output sequence, $\{w_k\}$, $$w_k = \text{median}\{Y_{k-d-h+1}^2, Y_{k-d-h+2}^2, \ldots, Y_{k-d-1}^2, Y_{k-d}^2\},$$

with, e.g., h=4800 (to use 20 seconds of data), and d=240+480=720 (i.e., this median filter is delayed 1 second from the end of the 2 sec. foreground window, i.e., 3 seconds from the current time), so that $$w_k = \text{median}\{Y_{k-5519}^2, \ldots, Y_{k-721}^2, Y_{k-720}^2\}.$$

Then define $$B_{k+1} = \begin{cases} \lambda B_k + (1-\lambda)w_{k+1} & \text{if } r_k < C_2 \\ B_k & \text{if } r_k \geq C_2 \end{cases}$$

where $\lambda$ is a "forgetting factor" which controls the rate of exponential forgetting (where this factor is between 0 and 1), $r_k$ is the current ratio of the foreground "ictal index" to the background "ictal index," given by $$r_k = \frac{F_k}{B_k},$$

and $C_2$ is a threshold level used to disable updates of $B_k$ when $C_2$ is exceeded by $r_k$. For accurate, real-time detection of seizures, the ictal signal should not be allowed to affect the background signal from which the seizures are distinguished. Accordingly, to further improve the detection method, the constant, $C_2$, above was introduced to disable updates of the background ictal index, $B_k$, whenever the ratio, $r_k$, is large (i.e., exceeding $C_2$). Failure to disable these updates would allow unwanted rapid growth in the background ictal index during a seizure, resulting in a loss of ability to measure seizure duration, and a degradation in the ability to detect latter seizures (or the regeneration of a single evolving seizure) when these events are closely spaced in time. This enhancement of the method is especially important when one wishes to detect the end (and hence the duration) of a seizure in addition to the onset time.

Figure 5B:
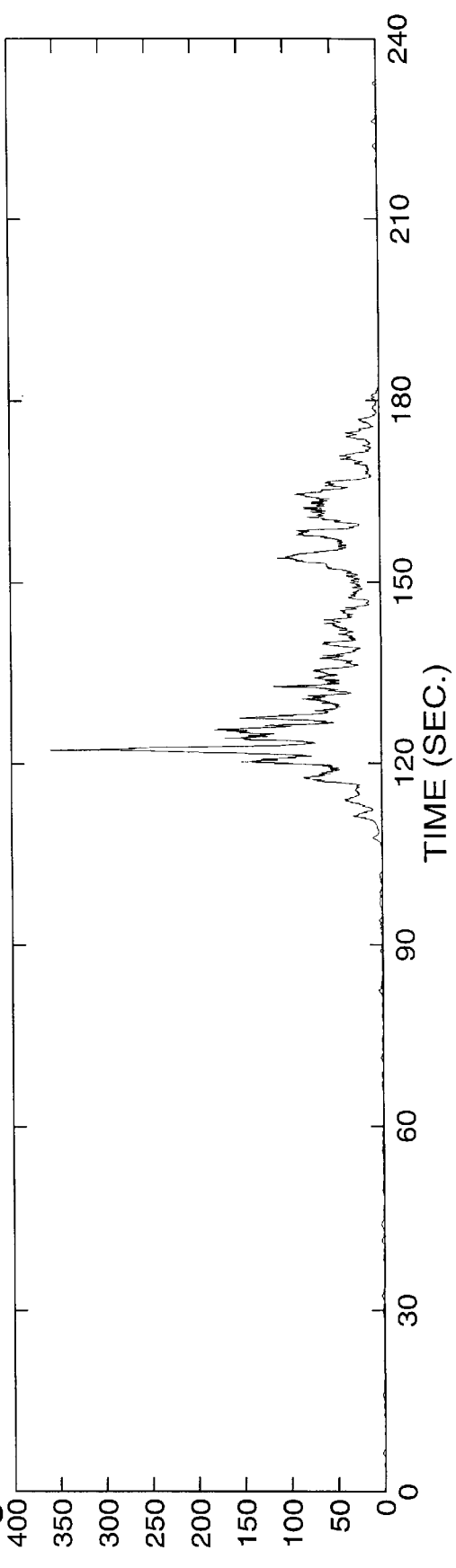
FIG. 5B is a graphical illustration of the dimensionless ratio of a 1 second foreground median filter and a 20 second background delayed median filter applied to the squared, FIR-filtered signal shown in FIG. 5A in an embodiment of an invention.
Figure 6A:
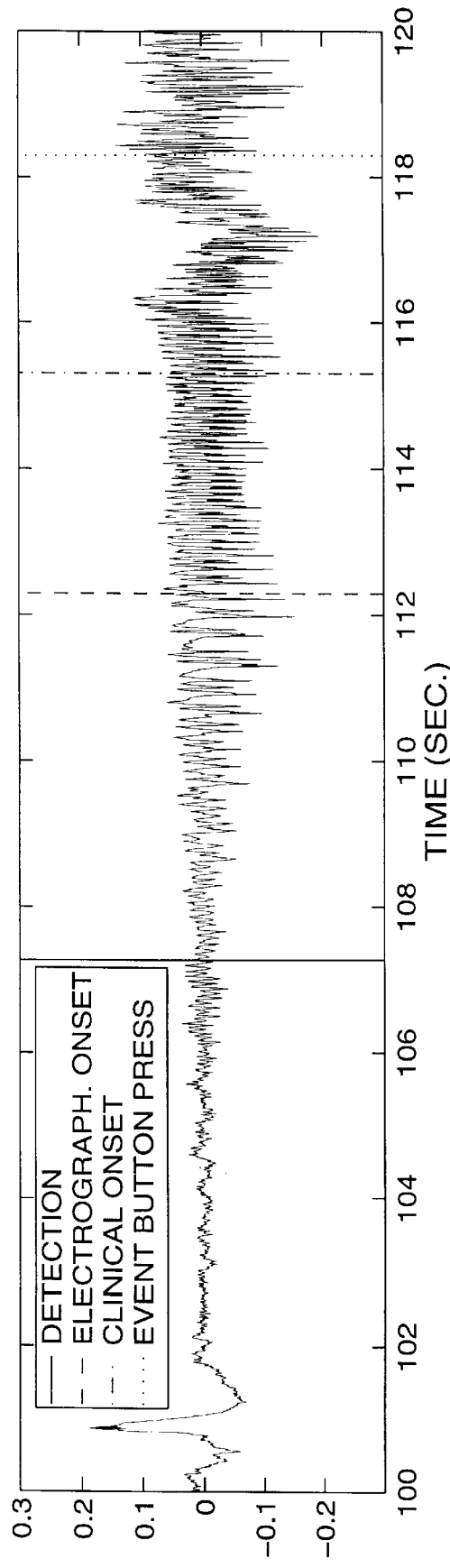
FIG. 6A is a graphical illustration of the part of the ECoG signal from FIG. 4 during which the clinical and electrographic seizure onset and subject activation of the event button occurred, and during which the apparatus of FIG. 1 detected the seizure.
Figure 6B:
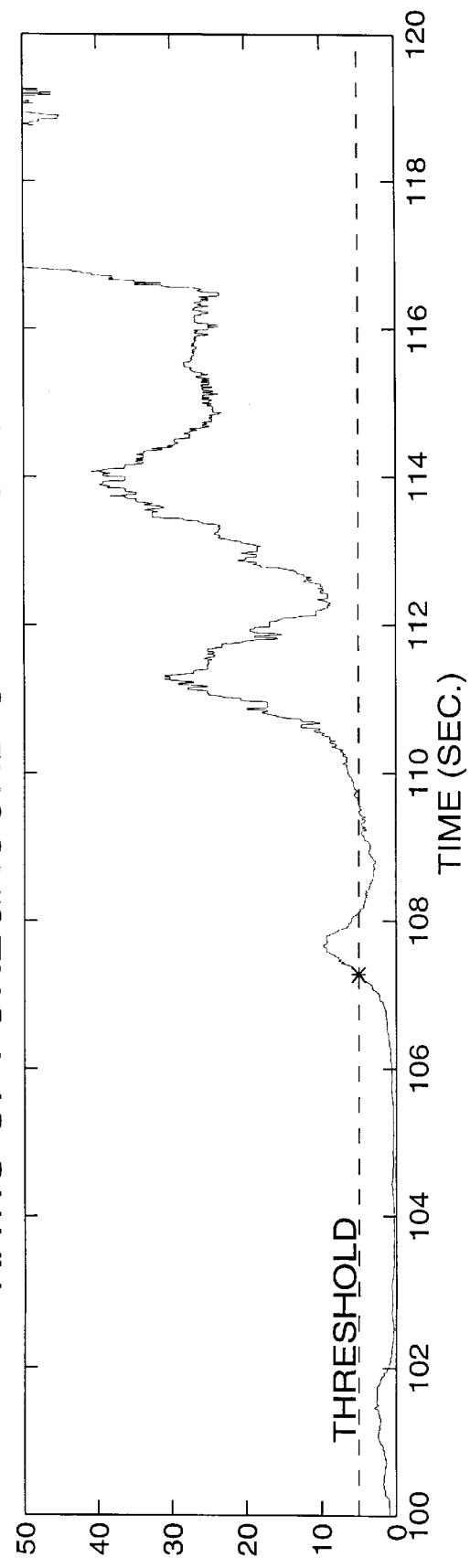
FIG. 6B is a graphical illustration of the output of the seizure detection embodiment as presented in FIG. 5B but restricting the time window to that time period corresponding to the signal of FIG. 6A.

A seizure detection is immediately signaled when the ratio, $r_k$, exceeds $C_1$, which is the detection threshold. When the foreground and background median filters are 1–2 sec, and 20 sec, respectively, nominal preferred values for the above defined constants are $C_1=20$, $C_2=5$, and $\lambda=0.9997$. Also note that because the ratio, $r_k$, is dimensionless, the threshold may be set without regard for the units used in the particular signal being monitored. FIGS. 5B and 6B show the graph of this ratio, when the method is applied to the signal of FIGS. 4 and 6A. In this example, the method detects the seizure 5 seconds prior to the electrographic onset (as determined independently by a trained epileptologist), 8 seconds prior to the clinical onset of the seizure (as determined by review of the videotape record by the same epileptologist), and 11 seconds prior to the patient's activation of an event button (signaling the beginning of the seizure according to the patient), as FIG. 6B illustrates.

By varying the lengths of background and foreground, the accuracy and speed of detections may be adjusted to improve performance as desired for a particular application of the method. The preferred embodiment constitutes a substantial improvement in the state of the art in both speed and accuracy of detection. In addition, the adaptability of the system's parameters provide flexibility and improved performance for a variety of applications. For example, if the speed, but not the accuracy of detection is the overriding factor for success in seizure abortion, then a decrease in the foreground window length is one way to achieve this result. If, on the other hand, this method is to be used in a device to destroy the part of the brain from where the seizures originate, then maximal accuracy (and not detection speed)

is needed to avoid damaging healthy tissue. This can be accomplished by increasing the length of the foreground window.

The novel use of order-statistic filtering in this invention and, specifically, a median filter, to characterize the ictal activity in the foreground significantly improved the accuracy of seizure detection by enabling discrimination between ictally organized and non-organized epileptiform activity. The further additions of time- and state-weighted averaging, and the formation of a ratio comparing the level of ictal activity in the recent signal (foreground) to that which is normally present during interictal (non-seizure/background) periods, among other ideas (described below) have enabled the present invention to provide improved results not only in speed, but also in accuracy and adaptability. Additionally, the method allows for online learning and adaptation as discussed in later sections.

As the signal from each individual sensor is monitored in the aforementioned manner for the detection of seizures, spatio-temporal correlations between the ratios simultaneously computed for multiple sensors which may be obtaining signals of the same class (e.g., all ECoG, or different classes (e.g., ECoG, EKG, and blood chemistry) can then be used, if necessary, to increase sensitivity and specificity of the algorithm, e.g., by allowing for sensor and signal dependent threshold settings and the use of multichannel information in both seizure detection and artifact rejection. Those skilled in the art recognize that external sensors produce a lower signal to noise ratio than implanted sensors. This drawback is particularly prominent for sensors placed on the scalp for EEG monitoring due to volume conduction and low-pass filter effects on the cortical signal caused by the structures surrounding the brain. Furthermore, the signal recorded from the scalp may be delayed from that directly recorded from the brain. In order to compensate for these drawbacks, the following strategies have been adopted (individually, or in combination):

1) Prefiltering of the scalp signal and other inputs to extract the useful signals (e.g., separate cortical voltage potentials from artifacts).

2) Artifact pattern recognition. Artifacts, defined as signals that are not the direct product of cortical neuronal activity occur during normal activity and also during seizures. During their clinical component, seizures generate a host of artifact signals that, for a given individual, may be highly stereotypical in their spectral and spatio-temporal characteristics and as such are distinguishable from cortical seizure activity. These artifacts, which correspond to body, mouth, or eye movements, etc., are first recognized by comparison with artifacts that have been catalogued into a general library according to their characteristics. As these artifacts are identified, their temporal evolution is tested for conformance to a pattern of artifacts stereotypic of that individual's seizures.

3) Use of other signals such as EKG, respiratory rate, magnetic fields, thermic potentials, concentrations of chemicals, recordings from a dynamometer or accelerometer attached to the patient or bed, etc. for use in seizure detection or prediction.

Once a seizure has ended, there is usually a decrease in signal power in certain frequency bands. This decrease is dependent upon the intensity and duration of the seizure, among other factors. The method/device tests for and measures the duration of any loss of power following a large increase (such as that which occurs with seizures), and the results of these tests are used to retrospectively assess the accuracy of seizure detection. For instance, a large sustained increase in power, without a subsequent power decrease in certain bands, would be routinely subjected to off-line review.

The Adaptive and Evolutionary Nature of the Method

Large scale validation studies have proven that the above-detailed embodiment for seizure detection is both highly sensitive and specific. However, to account for possible intra- or inter-individual signal variability, and to further improve performance as needed, a number of additional steps have been implemented which allow the system to learn and adapt on and offline. These steps can be grouped into the following categories:

(1) adaptive signal acquisition methods, (2) intelligent parameter adjustment, and (3) adaptive use of detection and prediction information.

The first step in adapting the method to a particular subject or application consists of selecting the appropriate set of signals to be monitored, and controlling the manner in which these signals are acquired. Although the detailed example above makes use of signals consisting of electrical potentials (EEG/ECoG) sampled at 240 Hz and digitized with 10 bits of precision, in some cases one may, as discussed earlier, vary the analog to digital conversion parameters, or use the analog signal itself, in order to ascertain various characteristics of the signal which may be important in the subsequent analysis. For example, sampling rate may vary continuously with the frequency content of the signal, increasing with the slope of the wave (differential sampling); the steeper the slope, the higher the sampling rate. In addition, online signal quality control methods can be used to detect various forms of signal degradation and warn the user or others. For example, the system can produce an output indicating the presence of a large quantity of 60 Hz activity, or abnormally high "clipping" in the analog to digital conversions, etc. Moreover, in many cases it is advantageous to record signals from other sites (or organs) in addition to the brain or its encasing structures, and to analyze biological signals other than EEG/ECoG, including, but not limited to, (1) other electrical potentials (AC or DC), (2) EKG, (3) EMG, (4) respiratory rate, (4) concentrations of glucose, free radicals, or other substances (e.g., neurotransmitters) in the brain, blood or other tissues, (5) magnetic fields, and (6) brain temperature. It is also important to note that while, for the sake of clarity, attention is primarily focused on data from a single sensor in the detailed example above, in practice the method can be applied to signals from a large number of individual sensors and combinations of sensors (e.g., a weighted sum of the electrical potentials between a given sensor and all other sensors) simultaneously (i.e., in parallel), monitoring spatio-temporal correlations of the resulting outputs.

The parameters of the method may be adjusted as needed. Parameters such as foreground and background window length, filter shape and type, time-weight, and threshold settings may be adapted on or offline to the particular subject and application. For example, if data exists containing a prior seizure for a given subject, then one can process this data to realize a filter adapted to any known signal characteristics or seizure "fingerprint" of that subject. A filter with the spectral characteristics of its impulse response matching the typical PSD at seizure onset for this subject, can be used to initialize the adaptive filtering procedure, thereby improving the sensitivity and specificity of the algorithm for that subject. The FIR filter may also be adapted to the particular location of the sensor, or the type of signal being monitored. For example, when monitoring posterior electrodes (e.g. occipital), the preferred filter is designed to recognize and de-emphasize irrelevant signals in the alpha range (8–13 Hz with normal reactivity), when its power is below a given percentile. While spectral characteristics of seizures for a given subject may differ from those analyzed for the design of the generic filter, this method, by virtue of its adaptability, is well suited to prediction and detection of seizure patterns with a wide range of spectral and other relevant characteristics.

To increase computational efficiency, one may also use a stable infinite impulse response (IIR) filter (also known as an auto-regressive moving-average or "ARMA" filter) in place of the FIR filter. Such filters use a linear combination of past filtered signal values in addition to present and past input signal values to compute each new filtered signal value. That is, given IIR filter coefficients $A=[a_1\ a_2\ a_3\ a_4\ \ldots\ a_n]$, and $B=[b_1\ b_2\ b_3\ \ldots\ b_m]$, and input signal $\{x_1, x_2, \ldots, x_N\}$, we compute the sequence $\{Y_N\}$ using the recursive formula:

$$Y_N = -a_1 Y_{N-1} - a_2 Y_{N-2} - \ldots - a_n Y_{N-n} + b_1 x_{N-1} + \ldots + b_m x_{N-m}.$$

This feedback of the filtered signal allows the IIR-filtered output to be produced with fewer computations and shorter delay time.

The FIR filter step utilized in the preferred embodiment example is a special case of more general adaptive filtering methods which may be employed to decompose the signal, extracting and enhancing signal activity indicative of an ongoing or impending change of brain state. For example, one may allow the FIR filter coefficients (and order) mentioned above to vary with time as a function of the current brain state, to increase the accuracy of the method under certain conditions. The method can use a different filter when the subject is in slow-wave sleep, from that which is used during vigorous exercise, since the characteristics of the background signal and noise level/type, from which a change is detected, are markedly different in these two states. Those skilled in the art are aware of many known methods of digital signal processing which can be used to achieve such online adaptation (e.g., "active noise cancellation"). In the presently preferred implementation, one begins with a generic filter (as above), that allows for the detection of seizures which may begin in a wide range of frequency bands. As the input signal evolves over time in the non-seizure state, windowed power spectral density (PSD) estimates of the signal can be successively computed, and a PSD representative of the recent (or entire) signal history may be obtained, together with confidence intervals, a median, min, max, and other percentiles, etc. This representative PSD is then used to modify the current filter's impulse response, in accordance with the newly acquired subject-specific and state-representative "background" information to improve detection of subsequent state changes. Interictal PSD's which do not fit any predetermined ictal pattern, but which are sufficiently different from the background PSD, may be archived and reviewed; these and parameters which may be computed from the PSD (see Appendix 2), may be used as templates for detecting other state changes, precursors to state transitions, and for signal quality control. Archived seizure segments can also be used in the online adaptation of this filter, focusing attention on the frequency bands of past seizures which are maximally differentiated from their respective interictal segments. Those skilled in the art will further recognize that several methods exist for online filter design from a given PSD, e.g., the method of Parks-McClelland. In addition to filters whose design is mainly based on the PDS, phase, shape and other characteristics (e.g., neurally-based filters or other signal-shape filters) can be used to realize new filters as necessary.

Parameters can be adjusted in this method, to detect ictal activity on a wide range of time scales and sensitivities. In particular, by reducing the length of the foreground window from the 2 second length used above to 0.2 seconds, individual spikes can be detected with this method. The detection of these spikes as they occur enables the creation of a biofeedback system in which the subjects are made immediately aware of epileptiform activity in their brain (e.g., by an auditory transduction of the abnormal signal activity for auditory pattern recognition). Such a system can be used to teach the subjects to control or eliminate their abnormal own discharges.

The thresholds, $C_1$ and $C_2$, can also be adjusted online, based on accumulated statistics and functionals of the computed ratios, $\{r_k\}$, over long time periods, including the ratio values attained during seizures, together with the maximum and minimum values reached interictally.

Finally, the ways in which the system uses detection and prediction information can be made adaptive as well. For example, a warning alarm could have a feedback mechanism to detect background noise, and adjust its output signal accordingly—from a vibration when in the library to a loud tone when on an airport runway. As another example, changes in stimulation parameters for intervention or seizure abortion can be made based on a history of therapeutic effectiveness.

Other Embodiments of the Seizure Detection Method

The task of seizure detection requires near-simultaneous temporal-frequency localization of the signal. Real-time seizure detection imposes the additional demand of high processing speed.

The use of adaptive filtering in the preferred embodiment is ideally suited to meet these demands. Those skilled in the art will appreciate that a variety of other methods can be used for nearly-simultaneous temporal-frequency localization, including the windowed Fourier (or Gabor) transform (WFFT), the wavelet transform, the Hartley transform, and the Wigner-Ville transform. Any of these methods can be used to extract or enhance the ictal part of the signal from the entire signal as in the first step of the adaptive filtering method.

In addition, a number of other transforms can be used to accurately and rapidly extract and enhance the ictal portion of the signal. We give two examples:

1. Windowed correlation integrals: Embed the original (windowed) signal in a higher-dimensional space using the method of time-delays, a standard technique in nonlinear dynamics and statistics. Then count the number of pairs of points whose separation is less than some critical distance (this is called the sample correlation integral). Monitor this statistic as a function of time. Ictal activity is indicated when the number of such pair falls by an order of magnitude or more. Higher order correlations can also be used.

2. The windowed "kinetic energy," defined as follows: take the first difference of the time series represented by the signal, re-embed this derived time series with a suitable lag time, then choose a window size (time interval); in each window, and compute for each window the sum of the squared lengths of all the vectors, and monitor this statistic as a function of time.

Both methods are robust against changes in the control parameters such as embedding dimension, delay time, and window length. In particular, both have been effectively employed with short window lengths and embedding dimensions as low as 3, enabling real-time monitoring, detection and prediction. Both of these methods measure what might be characterized as a relative dispersion, at a certain scale, of the points on the re-embedded trajectory. As such, they are remarkably insensitive to small fluctuations in the position of the points, which in turn means that these methods are extremely robust against the contamination of the signal by noise. For example, using method 1, only a slight decrease in sensitivity occurs when the signal is contaminated by sufficient Gaussian noise to reduce the signal-to-noise ratio to 5 dB.

It should be noted that the transforms listed in this section are also useful for preprocessing signals when little is known a priori about the frequency bands of interest or the time scale of changes. In particular, these methods can be used as initial screening tools in determining frequency bands in which changes are correlated with particular changes in brain state. Additional background details regarding the Fourier and wavelet methods may be found in Appendix 2.

Coherence analysis, and higher order spectra and cumulants, etc., also provide additional important information regarding signal frequency changes over time.

The presently preferred computer program for seizure detection shown in Appendix 1 performs on-line median filtering, updating the moving foreground and background median filters at 240 Hz. For this task, the program makes use of circular doubly-linked lists. For certain applications (e.g., to conserve processing resources when a large number of signals are being monitored simultaneously), these computations may be performed less often using well known batch sorting algorithms (e.g., Quicksort), to compute the median in moving windows. One may also replace the median filter by a similar order-statistic filter, or with some other measure of central tendency (e.g., α-trimmed means). For computation of the background index described above in the case when a very large background window is desirable, one may instead compute the sequence, $\{B_k\}$ using the exponentially forgetting average of the median of periodically sampled foreground values. For example, the background value can be updated once per second by first computing the median of the foreground values that occurred at each of the last 300 seconds, then adding this result (properly weighted), to the previous background value.

Another preferred embodiment of the above methodology consists of the analog implementation of the digital methods described herein. Those skilled in the art will appreciate that every step of the method presented herein can be implemented in analog. This fact is important in the context of miniaturization and the development of implantable devices, since analog devices generally require significantly less battery power to operate and, thus, last much longer.

An Application of the Seizure Detection Method to Imaging

The seizure detection method applied to a signal recorded from a particular sensor produces a dimensionless ratio representing the current level of ictal activity present at that corresponding location. As part of the present invention, a new "seizure imaging" method was developed based on this seizure detection methodology. The seizure image is obtained using a contour plot of the brain regions which achieve the same seizure ratio ("equiictal"), and tracking the temporal and spatial evolution of this ratio; the contours are directly obtained by interpolating these ratios over both space and time.

FIG. 7 illustrates the application of this seizure imaging method to a seizure recorded simultaneously from two implanted needles each containing 8 contacts. Contacts 1–8 recorded activity from the left, and contacts 9–16 recorded activity from the right amygdalo-hippocampal regions. The times of seizure detection (solid line, 107 sec. after an arbitrary initial zero time), electrographic onset (dashed line, 112 sec.), clinical onset (dot-dashed line, 115 sec), and event button press (dotted line, 118 sec.), are annotated. This graph illustrates that the seizure originates from contact 12, then weakens somewhat, followed by a more widespread resurgence at neighboring contacts, first in those more anterior (9–11), and then later involving the more posterior right temporal contacts (13,14). The onset of activity in the left hemisphere begins at 156 sec. on contact 4, but then spreads to contacts 1–3, and 5 within 3 sec, and to the posterior contacts 6–8 four seconds later. Ictal activity on the left is evident for 15 seconds after the cessation of right temporal involvement. This particular imaging technique can be very helpful to the clinician in spatio-temporal localization of seizure activity and, in particular, in localization of the site of origin of the seizure and characterization of the pattern of spread.

It has been found as part of the present invention, through the application of this seizure imaging method, that seizures from the same subject usually have a high degree of spatio-temporal congruency of ratio intensity. Accordingly, such images and the pathways of ictal propagation which they depict, can be used in the analysis of spatial correlations in the outputs of the simultaneously evolving, single-channel detection ratios computed as described in the preferred embodiment of the method. Specifically, any detected seizure may be compared in terms of its spatial evolution, propagation speed, and intensity evolution (including, e.g., the trajectory of maximal absolute and relative intensities), with similar information from prior ictal events, and the degree of conformance can be quantified and used in assessing whether (a) the detection was a seizure, or (b) seizures originate from one or multiple sites. These methods may also allow therapeutic intervention at the sites to where the seizure spreads, when treatment at the site of origin is of limited efficacy.

Those skilled in the art will appreciate that other quantities computed from the input signals (not just the above-mentioned ratios) can have their spatio-temporal evolution depicted via similar imaging techniques, and that a variety of different existing interpolation techniques may be employed.

A Method for Detection of Epileptiform Discharges or Spikes

The method described herein for detection and classification of spikes, is based on a new method developed as part of this invention for computing relative sharpness of the signal as it evolves, and comparing it to the sharpness of other waveforms. In prior art methods, the sharpness is computed at each successive signal maximum or minimum using the numerical second derivative at that point, or by connecting adjacent signal minima and maxima with straight lines and measuring the resulting angles. These approaches, however, are inaccurate because they ignore signal characteristics near each peak, and rely too heavily on a small number of digital points approximating the underlying continuous signal, using too few points near the peak (the region of primary interest) and too many points far away from the peak. The present invention includes a new method for computing this sharpness using what we shall call a "least-squares acceleration filter" (LSA filter), which overcomes these limitations of prior art. This method can be used independently, or as an improvement to existing methods, many of which rely heavily on relative signal sharpness in their detection of spikes.

This method consists of first fitting a function to the data surrounding the point at which the sharpness is to be computed, and then determining the sharpness of the fitted function. The preferred function for use in this fit is a parabola, and the preferred criterion for the fit is the minimization of mean-squared error of fit (least squares). The parabola is used because its second derivative can be obtained from the computation of a single value (its leading coefficient), and no function evaluations (which can be computationally expensive) are necessary. Other performance criteria for an optimal fit could also be used. The choice of least squares is relatively standard, highly effective, and has been made computationally feasible here.

The computation of the sharpness (i.e., the acceleration) of the signal(s) at each data point has been reduced to applying a small order FIR filter to the data from that sensor. The output of this filter is equivalent to first computing the parabola which attains the optimal fit (in the least squares sense) to the data near the point in question, then computing the second derivative of this parabola, which is used as a measure of sharpness.

One may then obtain an index ratio of relative sharpness at a particular point in the signal by dividing this computed peak sharpness by, e.g., the median sharpness of all waves occurring in a moving background window of the signal. If the absolute value of the resulting dimensionless relative sharpness exceeds a given threshold, $C_3$, then the wave is classified as a potential spike. The preferred nominal value for $C_3$ is 50, but may be adjusted as needed. When a potential spike is detected, the polarity of the discharge may then be obtained from the sign of the computed acceleration.

Figure 8A:
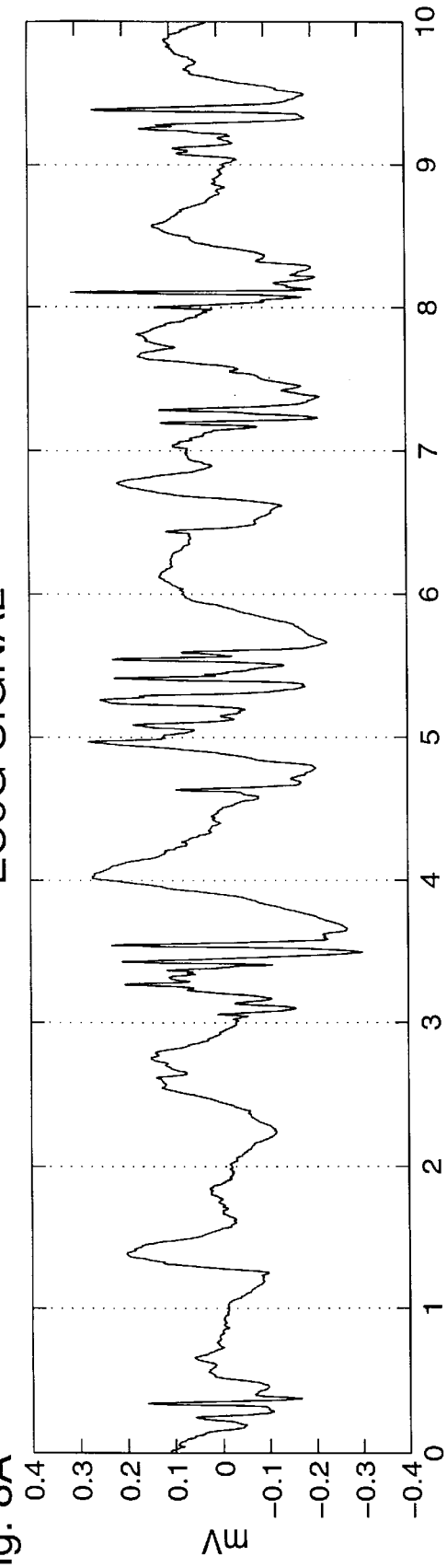
FIG. 8A is a graphical illustration of an ECoG signal which contains a number of epileptiform discharges.
Figure 8B:
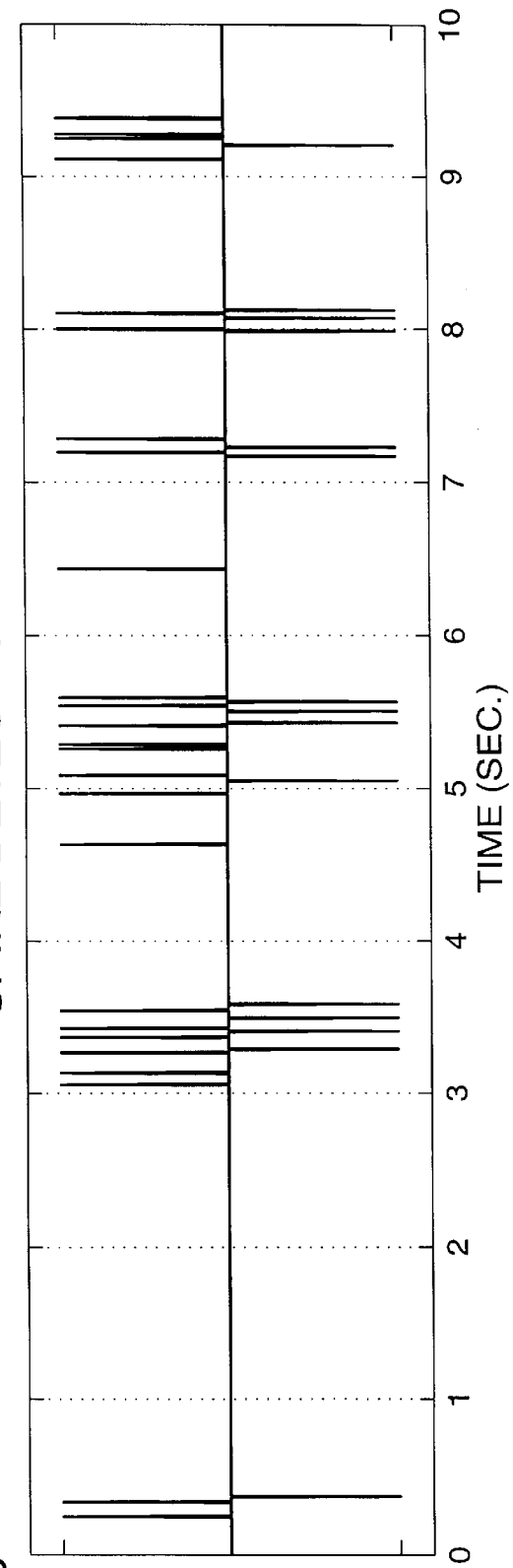
FIG. 8B is a graphical illustration of the output of first step of the spike detection embodiment; potential spikes with sharpness as computed by LSA filtering) exceeding a given threshold and their respective polarity (up or down) are identified.

FIG. 8 shows a 10 second segment of the ECoG signal containing a number of spikes, along with the resulting detections (and their respective polarities) made using this method. Now spatio-temporal correlations may be used to (a) reject artifacts, (b) group detected "spikes" into complexes, and (c) detect the occurrence of discharge patterns which may serve as precursors to seizure. Source code useful in accordance with the present invention is included in the microfiche appendix. Those skilled in the art will appreciate that genetic algorithms alone or in conjunction with neural network or fuzzy logic may be effectively used to analyze the spatio-temporal correlations of detected potential "spikes" for artifact rejection.

Prediction of Seizures through the Detection of Precursors

It has been found as part of the present invention that many patients have precursor signals that consistently precede the onset of both the electrographic and clinical components of their seizures. Three examples described below illustrate such precursors, present detailed methods for detecting them in real-time, and demonstrate their utility in seizure prediction.

EXAMPLE 1

Figure 9:
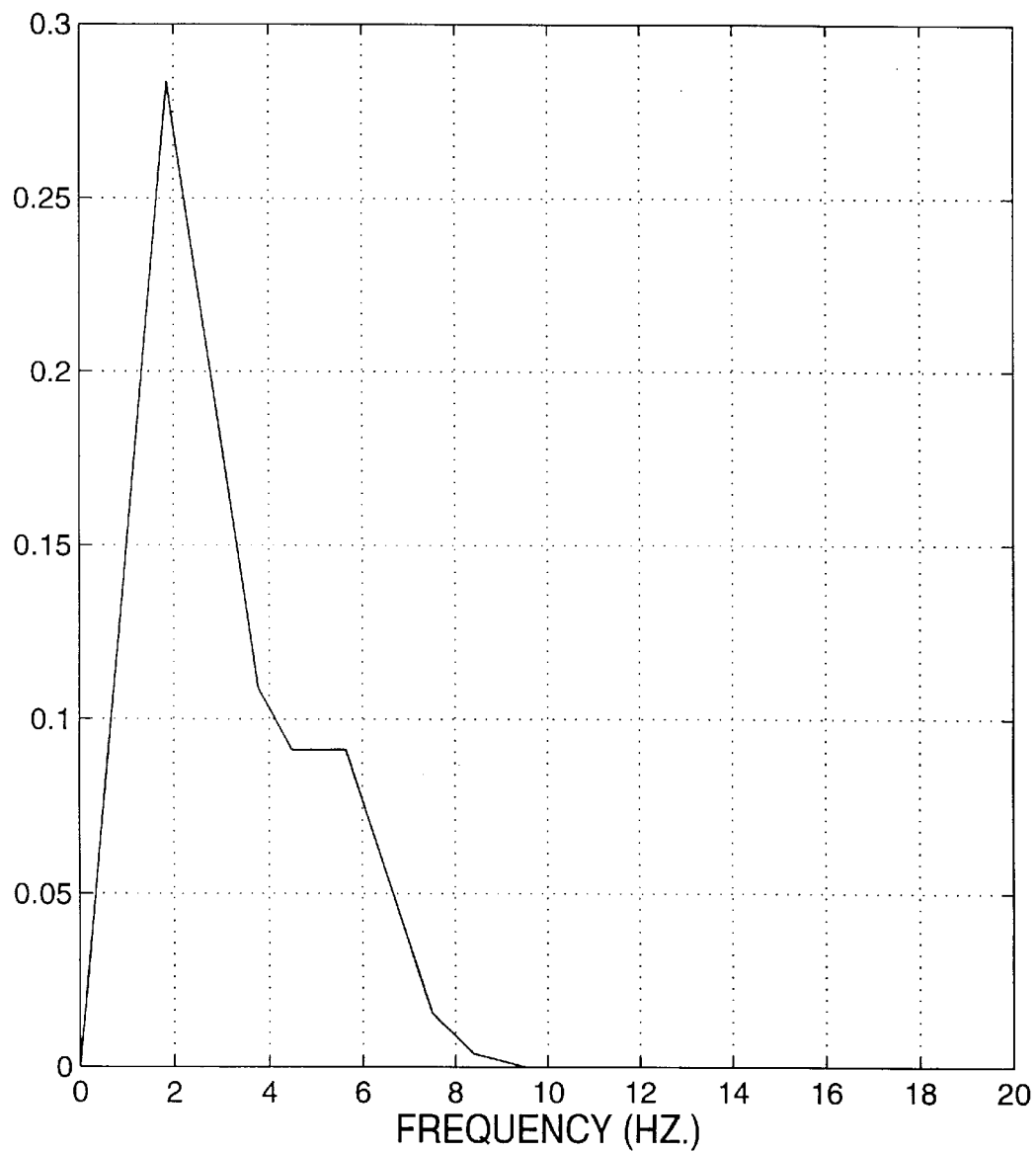
FIG. 9 is a graphical illustration showing the power spectral density (PSD) or the impulse response of the presently preferred IIR filter designed to be used in detection of the seizure precursor spikes as described in Example 1.

Often subjects have an onset of large energy, primarily low frequency, quasi-periodic epileptiform discharges which occur seconds to minutes prior to the electrographic component of a seizure. Such patterns are rare to non-existent in the interictal state. The following is a description of how the present invention may detect the occurrence of such a precursor:

First, a linear combination of the signals from relevant sensors is formed in a manner that enables the preservation of the polarity of each discharge so that there is no cancellation through superposition of waves. Then a filter designed to extract precursor spikes with patient-individualized shape is applied to this composite signal. A generic choice of filter for use in this step (when the signal is sampled at 240 Hz), is an IIR filter with PSD as shown in FIG. 9. This filter was designed using a data base of these precursor signals from various patients in a manner similar to that described earlier for the generic seizure detection filter. An IIR filter is preferred here instead of an FIR filter because of its advantages in filtering into such low frequency bands as that required here. The output of this filter is then squared, and, as in the seizure detection method, a background signal is computed by applying a 20 second median filter to these squared values, and then exponentially forgetting (slowly) the result. The relevant spikes are then identified by detecting the instant that the ratio of the current filtered signal (squared) divided by the background signal value exceeds a threshold value, $C_4$. Since these spikes are now individually detected, the method then tests for their occurrence in a particular rhythmic manner which is highly correlated with a later onset of the electrographic and then clinical components of seizure. Specifically, we impose "periodicity constraints" which test if there is at least $t_1$ seconds and at most $t_2$ seconds between spikes, and that at least N spikes occur in succession according to these spacings before a detection is signaled. The preferred nonadaptive settings of the above constants are $C_4=100$, $t_1=1$, $t_2=10$, and $N=2$. Each of these parameters (and the filter employed) can be adapted to patterns which may known a priori, or learned on-line for a particular subject via retrospective analysis of previously detected seizures.

FIG. 10 presents a graph of an ECoG segment recorded from one of the subjects that exhibits this particular precursor, and the time of precursor detection using this method is annotated, along with the onset times of the electrographic and clinical components of the seizure. This method has produced a prediction of clinical onset an average of 54 seconds prior to its occurrence, and a prediction of electrographic onset an average of 42 seconds prior to its occurrence. The detection of this precursor has been followed by a seizure within two minutes in 100% of cases analyzed to date.

EXAMPLE 2

As part of the present invention, it has been found that signal attenuation or "quieting" precedes, by up to tens of seconds, the onset of the clinical and electrographic components of seizure in many subjects. In those that exhibit this preictal quieting, the application of the following preferred method to detect the onset of this attenuation results in a prediction of the electrographic and clinical seizure components.

For any signal, $\{X_t, t \geq 0\}$, the average signal energy over the interval of time, $t_1 \leq t \leq t_2$, is given by $$A(t_1, t_2) = \frac{1}{t_2 - t_1} \int_{t_1}^{t_2} X_s^2 ds.$$

The average signal energy, $E_t$, in a moving time window of length T seconds is given by $$E_t = A(t-T, t) = \frac{1}{T} \int_{t-T}^{t} X_s^2 ds,$$

which can be computed recursively and efficiently online using the formula $$E_{t+\Delta t} = E_t + A(t, t+\Delta t) - A(t-T, t+\Delta t - T)$$

or $$E_{t+\Delta t} = E_t + (X_{t+\Delta t}^2 - X_{t-T}^2)/\Delta t.$$

The long-time average energy, $H_t$, used as an adaptive background value against which energy changes are measured, is given (recursively) by $$H_{t+\Delta t} = \lambda H_t + (1-\lambda) E_{t+\Delta t},$$

with the preferred value of lambda being slightly less than 1. The above recursions can be initialized using the formulae:

$$E_T = \int_0^T X_s^2 ds, \quad H_t = E_T.$$

Now a ratio, $R_t$, is computed as $$R_t = \left[\frac{E_t}{H_t}\right]^{-1},$$

and a precursor detection is made the instant that this ratio exceeds a threshold value $C_5$. Note that an increase in this ratio corresponds to a decrease in average signal energy. Preferred nominal values for the parameters in this method are T=5, and $C_5$=5, but these again may be adapted to particular subjects. This method has produced a prediction of clinical onset an average of 23 seconds prior to its occurrence.

FIGS. 11 and 12 present a graph of an ECoG segment recorded from a subject that exhibits this particular precursor, and indicates when the detection is made using this method relative to the clinical and electrographic onset times of the seizure. The detection is made on the graph 278 seconds after an arbitrary zero, which is 15 seconds prior to the independently determined electrographic onset, and 19 seconds prior to the time of clinical seizure onset.

EXAMPLE 3

It has been found as part of the present invention that, for some subjects, certain sudden changes in the power spectral density (PSD) of the signal may be used to predict an impending seizure onset. For example, a sudden significant drop in the median frequency of the signal (defined in Appendix 2) is a consistent precursor to seizure for some subjects. The following is a description of the preferred method for detecting the occurrence of such a precursor:

Begin by computing the median frequency of the particular signal of interest in moving windows of length $T_1$ (as described in Appendix 2). Compute a background median frequency using an average of the median frequency values in a moving window of length $T_2$. Then compute the ratio of the background median frequency divided by the median frequency in the current $T_1$ second window. If this ratio exceeds a threshold value $C_6$, a detection of this precursor is immediately signaled. The preferred nominal/non-adaptive choices of parameters are $T_1$=256/240 sec. (approx. 1.067 sec.), $T_2$=60 sec., and $C_6$=5.

Figure 13A:
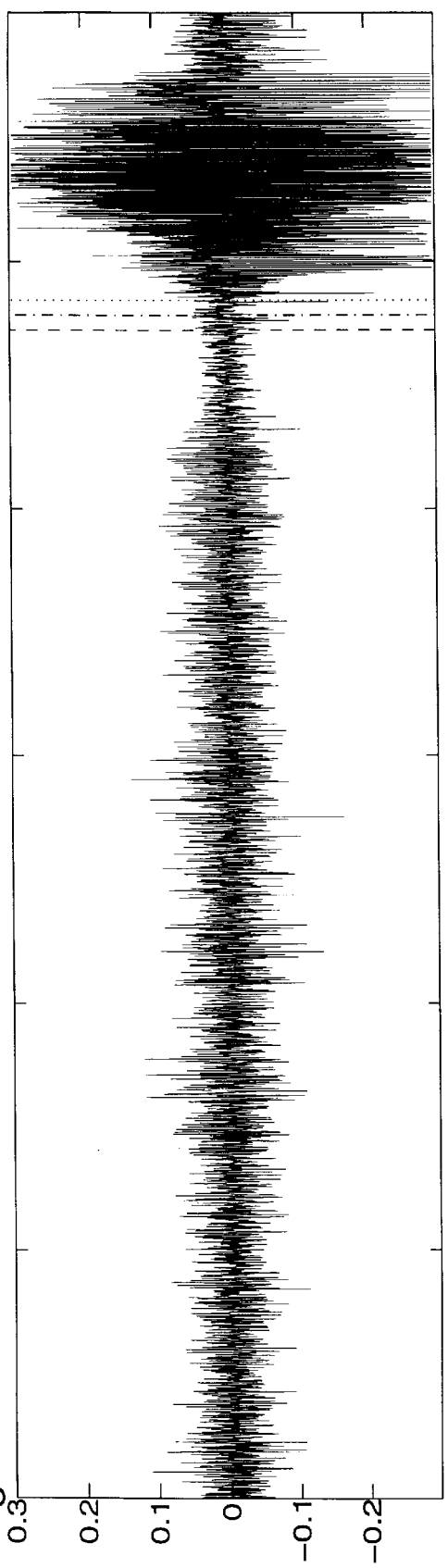
FIG. 13A is a graphical illustration of an ECoG signal of a subject which contains another seizure precursor signal (a rapid drop in median frequency, as detailed in Example 3). The times of the electrographic onset, the clinical onset, and the event button press by the subject are annotated.
Figure 13B:
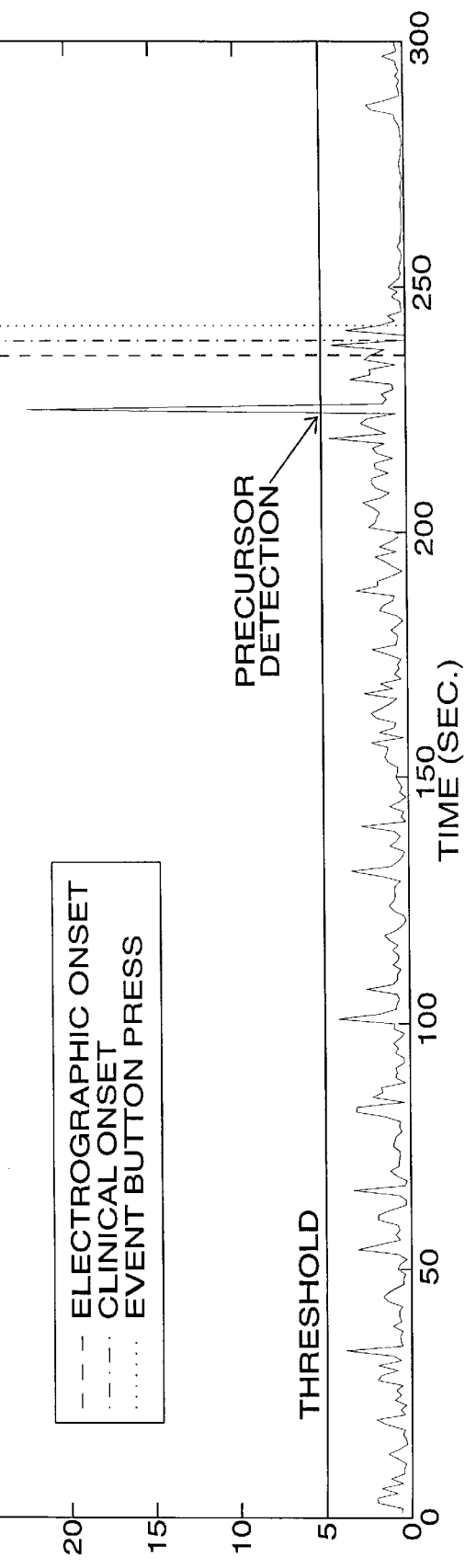
FIG. 13B is a graphical illustration of the result of applying the embodiment of the invention for detection of this particular seizure precursor to the signal presented in FIG. 13A. The electrographic and clinical seizure onsets, and the time of event button press are also annotated, as well as the time of precursor detection.

FIG. 13A shows a 5 minute segment of ECoG data which contains a seizure in the last minute. The times of electrographic and clinical seizure onset, and the time at which the event button was pressed are annotated (dashed, dash-dot, and dotted lines, respectively). FIG. 13B shows the graph of the ratio described above over this 5 minute segment, with a detection occurring 12 seconds prior to the electrographic onset, 15 seconds prior to the clinical onset, and 18 seconds prior to the patient's pressing of the event button. In the example used in FIG. 13, it should be noted that there is some signal energy attenuation as well (the precursor described in the previous example), but that this is not used in the detection of the precursor described now.

Other precursors which may be relevant for predicting an impending seizure for a particular subject or group can be isolated using modern pattern recognition techniques. As mentioned previously, preictal or interictal patterns which are present in the output of our seizure imaging method (which uses spatio-temporal interpolation of the ratios or other relevant quantities computed at each sensor) are strong candidates for precursors.

Another useful method for determining precursor signals for a given subject or group makes use of waveform classification and cluster analysis, followed by pattern recognition techniques applied to the resulting sequence of waveform "labels." The following illustrates how this can be done. One begins by segmenting an arriving input signal into individual "waves." This can be done in a variety of ways, for example, one could define a wave as 512 consecutive data points, or, more adaptively, as the number of data points between 2 successive baseline crossings of the signal. As each new waveform is segmented, it can be extensively analyzed and subsequently classified into a (possibly evolving) library of distinct waveforms or "cyma."

For example, the duration, amplitude, number of baseline crossings, arclength, maximal sharpness, number of local maxima and minima, area bounded between the waveform and a horizontal axis, total power, and the fraction of power in a particular frequency band (and any number of other quantities) could each be computed (and, if desired, statistically normalized), with the resulting n measures used to form a vector in n-dimensional space quantifying that particular waveform (in this example, n=9). The distances (either Euclidean or non-Euclidean) between this new "point" in n-dimensional space and a library list of other "points" can then be computed and analyzed to see which waveform or "cymeme" in the library most closely resembles the new waveform. In this way, the input signal can be labeled as a sequence of cymemes (or indices into a list of waveforms), and the resulting "cyma" can be analyzed as described above for the occurrence of patterns which may serve as precursors to a given change of state. Such waveform lists can be constructed from available data using currently known methods of cluster analysis, and neural networks can be employed in making online or offline decisions classifying a given waveform. Specifically, we have successfully used a competitive learning network trained with the Kohonen learning rule and an adaptive learning rate which decreases over time for this task of classifying the sequence of n-dimensional points into groups. These analyses can be performed consecutively where, in each step, a different analysis method can be used.

Correlation Detection and Automatic Precursor Identification and Isolation

This section describes the preferred methods for automatic identification of signal characteristics which are significantly correlated with later changes of state in this subject's brain. This is based on correlational analysis and pattern recognition techniques applied to the signal recorded prior to each change of state. The transformations which apply to a given input signal or set of signals (e.g., FIR filtering, fast wavelet and Fourier transforms, etc.) decompose the input and present its information content in an organized and useable form. The original signal, and the product of these transformations are then automatically analyzed for the occurrence of patterns significantly correlated with detected changes of state.

Signal analysis for correlation may occur on-line, or off-line from signals previously recorded and stored in memory. Further, the analysis can be done on the basis of predetermined patterns or patterns developed through correlation analysis, or both. One may select the segments of signal for analysis which precede these changes of state with "markers" in some externally controlled way, or one may simply let the software accumulate correlations between "major changes" and precursors in an inclusive fashion for eventual use. It is also important to note that the process can either be done off-line using data obtained from the subject or putative patterns, or online by automated systems installed as part of the device.

The following is an example describing the use of correlations for determining average signal power. Let $b_{Ik}$ be the $I^{th}$ time coefficient in the $k^{th}$ wavelet basis expansion (see next section for more details), using a fundamental wavelet time scale dt. Let the average value of $b_{Ik}$ over an interval, chosen for illustration to be one minute, be denoted $<b_k(t)>$. This is an average over roughly $I_{max}=2^{-k/dt}$ values of I. The interval begins one minute prior to time t. Let $<p(t)>$ be the average power in the signal over the same time interval, and $<p>$ be the average power over many previous intervals, such as 100. Form the running deviation of coefficients from the average, $b_{Ik}-<b_k(t)>$.

Form the running deviation of the power from its long term average, $<p(t)>-<p>$. A correlation matrix $C_{It}(k)$ is formed by multiplying $$C_{It}(k)=(<p(t)>-<p>)(b_{Ik}-<b_k(t)>).$$

This matrix depends on the level, k, the time step within the interval, I, and the interval start time t. If there is no correlation between the signal and the power in a particular level k, then the matrix for that k value will be a random variable in the index I. If a persistent correlation begins at time t+I*dt, at some level k*, then the product will rise at point I* and stay large, up to statistical fluctuations.

Applying this procedure over many intervals of "normal" or background state, typical values of $C_{It}(k)$ will be fairly independent of I and t, and only depend on the level k. Distributions of these values are formed and evaluated. When $C_{It}(k)$ rises well above a statistically likely value it represents a correlation between $b_{Ik}$ and the power, $<p(t)>$, in that interval. In one application, restricting the analysis first to intervals marked t* where $<p(t*)>$ rises well above the background, one identifies the region of the seizure. Only the $C_{It}(k)$ values for the immediately preceding interval need to be kept in this case. Then by examining the correlations $C_{It*}(k)$ as a function of level k and time I, the level or levels k* where large correlations occur for I>I* can be determined automatically. The time for the precursor to predict in advance the seizure is found by computing $(I_{max}-I*)dt$. These values of k* and I* can be output and stored, leading to automatic recognition of precursors.

Another similar method is to train any assembly consisting of a number of logic elements with connected threshold rules (such as a neural network) to recognize correlations between the precursor signals, and the macroscopic change of state. In this case the correlations between precursors and state change may be automatically registered and analyzed without the intermediate step of forming correlation matrices.

The same technique can be applied to linear combinations of the signal after application of various signal filters, e.g., considering simultaneously derived wavelet coefficients from different levels of resolution after application of the discrete wavelet transform. One could also project the input signal(s) into various other bases (i.e., apply other signal decompositions) and monitor the resulting signal components as they evolve over time ("pattern recognition").

The Use of Genetic Algorithms and Genetic Programming in the Adaptation and Evolution of the Methods for Seizure, Spike, and Precursor Detection Genetic algorithms (GA) and genetic programming (GP) may be used as part of the overall strategy of algorithm adaptation and evolution in the methods for seizure and spike detection, and seizure prediction. The problem of detection and prediction of seizures is a highly complex one, due to the large intra- and inter-individual variability of brain signals interictally and ictally. The problem of selecting parameters such as filter coefficients, thresholds, window lengths, type of signals, etc. to optimize a particular performance criteria is ideally suited for the use of GA. In this method, parameter sets are assembled into chromosome-like strings which are interchangeable and form the "first generation." This first generation is evaluated by a fitness function which will assign a score to each element of the generation. After the scoring is completed, the "best" elements are saved and reproduced for the next generation, possibly combined together ("cross-over"), and/or new elements ("mutations") are introduced. This process of generation, reproduction and testing is repeated, until elements of the resulting generation achieve the desired level of performance for the particular application.

The following example illustrates how GA may be utilized to choose a time-invariant FIR that maximizes performance. The first generation consists of a group of bandpass filters, each with 2 Hz. bandwidth, of varying orders (but less than 240 Hz.), centered at odd integral frequencies between 1 Hz. and 119 Hz., and designed according to the Parks-McClelland method. The resulting sensitivity and specificity are measured when each filter is used in the seizure detection method presented herein (e.g., by computing the mean squared time between detection and the electrographic onset as independently scored by an electroencephalographer), and the best filters are saved and "reproduced" for the next generation. These filters are also combined together via cascading ("cross-over"), and new "mutation" filters of different bandwidths are added at random frequencies. Mutations may also involve randomly decreasing or increasing the order of certain filters from one generation to the next, but staying below the upper limit of 240, and/or using another filter design methodology. This evolution is continued until some stabilization is reached, or until the resulting performance achieves a high enough degree of sensitivity and specificity for the given data base.

Genetic programming, a form of program induction, enables the method/system to evolve (without external inputs or re-programming) based on internal fitness functions. GP may enable the method to self-learn and extract the most relevant and useful characteristics of the signal.

APPENDIX 2

Some Background Information on Mathematical Methods

This Appendix presents some background detail helpful in understanding the preferred methods of the present invention.

The Discrete Fourier Transform

It is well known that every discrete signal defined on evenly spaced discrete time points $\{t_0, t_1, \ldots, t_{N-1}\}$, where $t_k=2\pi k/N$, can be interpolated by a trigonometric polynomial which can be written as $$f(t) = \sum_{j=-M+1}^{M+\theta-1} c_j e^{ijt}, \quad (i = \sqrt{-1})$$

where $$\begin{cases} \theta = 0, M = (N-1)/2 & \text{if } N \text{ is odd} \\ \theta = 1, M = (N-2)/2 & \text{if } N \text{ is even} \end{cases}$$

and $$c_j = \frac{1}{N} \sum_{k=0}^{N-1} f(t_k) e^{-ijt_k}.$$

This discrete Fourier transform (DFT) represents a given signal (or "time series") as a superposition of sine and cosine waves with different frequencies and amplitudes. The number of Fourier coefficients is equal to the number of data points in the signal and reproduces (in some sense) the information contained in the original signal. In practice, the DFT is computed using the fast Fourier transform (FFT). Once the signal is decomposed into these fundamental frequencies, one may analyze the signal's components in separate frequency ranges (bands), and examine the coefficients for dominant frequencies. One generally computes an estimate of the power spectral density (PSD) from the Fourier coefficients in order to determine the dominate modes of the system. The simplest such estimator is the periodogram, which is a graph of the squares of magnitude of each of the Fourier coefficients, in order to see dominant modes of the system. As used herein, PSD means any of the estimators commonly employed in signal analysis.

The PSD of the signal $\{f(t_0), f(t_1), \ldots f(t_{N-1})\}$ is obtained from the Fourier coefficients, $\{c_j\}$, as $$p_j = \begin{cases} |c_j|^2 & \text{if } j = 0 \\ 2|c_j|^2 & \text{if } 0 < j < M + \theta - 1 \\ |c_{M+\theta-1}|^2 & \text{if } j = M + \theta - 1. \end{cases}$$

Here $p_j$ may be interpreted as the total power at frequency $w_j$ in the segment of signal which was transformed. There are M+θ different frequencies, $w_j$, at which signal power is computed, and these frequencies are evenly spaced between $w_0=0$ Hz, and $w_{M+\theta-1}=F_s/2$ (the so-called Nyquist frequency) which is half of the sampling frequency, $F_s$, of the signal (240 Hz above). The PSD contains precise frequency information about the given signal ("frequency localization"), but contains no information about the particular times at which a given frequency occurred. However, in the preferred applications, the time of a particular frequency change is important.

The windowed fast Fourier transform (WFFT) was created to address the lack of temporal resolution of the discrete Fourier transform; the signal is partitioned into successive segments or windows and the PSD in each window is computed, allowing the user to track changes in the frequency content of the signal window-by-window, i.e., in time. It must be understood, however, that the temporal resolution of the time of frequency changes in the signal is only on the order of the length of the window. Also, due to the discrete nature of the data, there is a degradation in the ability to accurately compute the full frequency content of a signal as the size of window is decreased since the number of frequency coefficients returned by the DFT is equal to the number of data points transformed (the window length).

An important application of Fourier methods in the present invention involves the analysis of the temporal evolution of various parameters associated with the frequency domain representation of the signal (i.e., the Fourier transformed signal). To accomplish this, one first computes the windowed fast Fourier transform (WFFT) of the signal obtained from a single sensor in a moving window of current data values and then the corresponding PSD estimate for each window. Then each PSD curve is converted to a probability density function (pdf) via normalization, and the resulting densities are treated as if they were characterizations of a non-stationary random frequency. To be more precise, suppose p(x) is a non-negative function defined on the interval, [0,L],(0<x<L). Without loss of generality, one may assume that the area under the graph of p(x) is equal to one, i.e., one may treat p as a pdf. If $\int_0^L p(x)dx \neq 1$, then one may simply redefine p via normalization, as $$\frac{p(x)}{\int_0^L p(x)dx}.$$

Considering p(x) as a pdf, one can compute statistics of the signal frequency distribution using probabilistic methods. In doing so, we obtain a number of parameters from the pdf in each window of time and monitor their absolute and relative temporal changes along with the time evolution of various relations between them. Some of the parameters computed are measures of central tendency in the PSD, including order statistics such as the median frequency (w.r.t. PSD), various moments of the pdf (e.g., the mean frequency), modal frequencies (i.e., the frequency with maximum power); and other parameters measure fluctuations in frequency in each window (e.g., the frequency variance, skewness, and kurtosis).

Precise formulae are now presented for some of these measures which are most commonly used. If p(x) is a continuous p.d.f. (defined discretely in this case) which is zero for x<0 and x>L, then the mean of the distribution (also known as the "first moment," or "expected value") is given by $$\mu = \int_0^L x p(x) dx,$$

the $n^{th}$ moment is given by $$\mu_n = \int_0^L x^n p(x) dx.$$

The variance of the distribution is given by $\mu_2 - \mu^2$. The median, $m_f$ of the distribution is defined by the equation $$\int_0^{m_f} p(x) dx = \frac{1}{2} 50\%.$$

Note that one may also define other percentiles (order statistics) in this manner. The median frequency of a signal in a given window of data is the 15 frequency which divides the area under the PSD in half. The mode, $M_f$, of the p.d.f. is given by $$M_f = \arg\max \{p(x)\}.$$

The modal frequency of the PSD (i.e., the frequency at which the maximum power occurs) is thus defined. FIG.

14A presents a signal comprised of 1024 points of ECoG data (about 4.267 sec.) recorded from a subject during an interictal (non-seizure) period. FIG. 14B illustrates the corresponding power spectral density (PSD) of the signal, showing the modal frequency, median frequency, and mean frequency of the signal, computed according to the above definitions.

One can use the modal frequency and variants of this concept to test the signal for rhythmicity, i.e., to detect segments of data which are nearly periodic. When this quasi-periodicity of the signal occurs, the power in the signal is concentrated at a few resonant modal frequencies. Many useful measures capable of detecting hypersynchronous patterns of neuronal firing often found in the recruitment and entrainment associated with seizures can be derived using a combination of measures such as those defined above.

For example, to detect hypersynchronous behavior of neurons focusing attention near 15 Hz activity, one can compute a frequency-biased functional of the modal frequency such as $$e^{\frac{-(M_f-15)^2}{10}}p(M_f),$$

where p is the PSD of the signal in, for example, a moving window of 256 points, and $M_f$ is the modal frequency for that window. One may then monitor the evolution of this measure for significant increases relative to background to produce a rapid detection of this type of signal activity.

This method for detecting rhythmic discharges in the signal can be further enhanced by weighing a measure such as that above by other measures of quasi-periodicity that can be computed from the signal itself (without first applying the FFT). For example, the reciprocal of the standard deviation of ten successive inter-zero-crossings (or interpeak intervals) increases dramatically in the event of hypersynchrony. The product of this measure with the one mentioned in the last paragraph provides an excellent method for the detection of this type of phenomena.

A number of other nonlinear functions based on these quantities (e.g., the product of the average energy and the inverse of the median frequency) can also be utilized as a means to obtain precursor information regarding an imminent change of brain state.

The Discrete Wavelet Transform

While the Fourier transform described above gives precise frequency localization of a particular signal, the discrete wavelet transform (DWT) has recently gained popularity because of its ability to provide useful temporal and frequency information simultaneously. The DWT expresses a given signal in terms of a basis consisting of translations and dilations of a single "mother wavelet," W(j). To be more precise, a given signal $\{x_j\}_{j=1}^N$, is expressed as $$x_j = \sum_{l,k} b_{lk} W_{lk}(j),$$

here $$W_{lk}(j) = 2^{\frac{-l}{2}} W(2^{-l}j - k)$$

The wavelet coefficients are defined by $$b_{lk} = \sum_{j=1}^{N} x_j W_{lk}(j).$$

The first "dilation" index of the coefficient controls the level of resolution of information, while the second "translation" index controls the temporal information contained in the coefficient. Representing a given signal in terms of wavelet coefficients rather than in the usual time domain is analogous in many ways to representing a musical composition as sheet music rather than looking at the graph of the sound waves through an oscilloscope as the piece is played. Each chord on the sheet music contains information about both the frequencies that are played and the time at which they occur.

As with the DFT, fast, efficient algorithms exist to compute the wavelet coefficients $\{b_{lk}\}$. The fast wavelet transform (FWT) which is based on the pyramid algorithm developed by Mallat makes the FWT even easier to compute than the FFT.

The FWT is applied to a given signal in windows of data of length $2^n$ points, for some prescribed value of n (e.g., n=6). The window size may vary based on a particular application and implementation. Use of the FWT may be desirable if one wishes to monitor signal changes in multiple frequency bands simultaneously and these desired frequency bands match those obtained by dilations of a particular mother wavelet. One may then group the wavelet coefficients by "level," i.e., by like dilation factor, ordered in each level according to their progression in time. The time between level 1 wavelet coefficients is $2^l dt$, where dt is the sample interval of the original signal. Hence, the level 1 coefficients contain the finest resolution (i.e., the highest frequency) information contained in the signal, and each lower level provides signal information at increasing time scales and decreasing frequency ranges. Level 1 corresponds to the smallest scale of resolution, and contains twice as many coefficients as level 2, which contains twice as many as level three, and so on. Recall that the EEG signal used in illustrating the preferred seizure detection embodiment described above was sampled at 240 Hz, so that a new data point appears roughly every 0.004 seconds. Computing the FWT using, e.g., 64 data points (0.267 sec.) results in 32 level 1 coefficients, 16 level 2 coefficients, 8 level 3 coefficients, etc. Thus for each level, there is a corresponding time series of wavelet coefficients representing the temporal evolution of signal power in a number of frequency bands, each higher frequency level "covering" a frequency band of width twice that of the next lower frequency level. FIG. 15 shows (the absolute value of) these series for levels 1–4 for a typical interictal segment of 512 data points (about 2 seconds) together with the original signal.

A Least Squares Acceleration Filter

In the method described earlier herein for computing the sharpness of a given waveform at a particular point, one first obtains an optimal parabolic fit to the data near the point in question. One then may use the second derivative (i.e., the acceleration) of the resulting parabola as a measure of sharpness at the peak. The criterion of minimizing the mean square error of this fit may be applied to obtain the best fitting parabola (in a least squares sense). This subsection provides the necessary mathematical details for accomplishing this step.

If $\{(x_j, y_j), j=1, \ldots, n\}$ are data points to be interpolated by the parabola, $p(x)=a_2 x^2 + a_1 x + a_0$, then the optimal coefficients $a_2$, $a_1$, and $a_0$ which minimize the mean square error $$\sum_{j=1}^{n}(y_j - p(x_j))^2,$$

over all choices of such coefficients, are obtained by solving the equation $$[a_2 a_1 a_0] = (X^+X)^t(X^+Y),$$

where $X_{ij}=x_i^{3-j}$, for $1 \leq I \leq n$, $1 \leq j \leq 3$, $Y=[y_1 \ldots y_n]^t$, and $X^+$ denotes the Moore-Penrose pseudoinverse of the matrix X. If we let $A=X^+X$ and $B=X^+Y$, then we have $A_{ij}=\Sigma_{k=1}^n x_k^{6-i-j}$, $1 \leq i, j \leq 3$, and the column vector $B_i\Sigma_{k=1}^n x_k^{3-i}y_k$, i=1,2,3. Once one solves this equation to obtain the optimal value for the leading coefficient, $a_2$, the second derivative of the parabola is equal to twice this optimal coefficient. The sign of this second derivative indicates the polarity of the potential spike as well, e.g., a negative second derivative indicates that the peak of the spike is a local maximum for the signal. The above formulae for computing $a_2$ may be simplified using the symbolic pseudo-inverse of the 3×3 matrix and subsequent matrix multiplication, resulting in the following formulae for a "least squares acceleration filter" which have been implemented to compute this sharpness measure in real time (i.e., the computation of the second derivative at a given point requires only p(p−1) floating point operations):

$a(p,dt)=dt^4 p(p-1)(2p-1)(3p^2-3p-1)/30,$
$b(p,dt)=dt^3 p^2(p-1)^2/4,$
$c(p,dt)=dt^2 p(p-1)(2p-1)/6,$
$d(p,dt)=dt p(p-1)/2,$
$e(p)=p,$
$A=ce-d^2,$
$B=cd-be,$
$C=bd-c^2,$
$D=aA+2bcd-eb^2-c^3,$
$E=[ABC]/D,$
$f=[0 dt^2 (2dt)^2 (3dt)^2 \ldots ((p-1)dt)^2],$
$g=[0 dt 2dt \ldots (p-1)dt],$
$h=[1 \ 1 \ 1 \ \ldots \ 1],$
$F=2E[f^t g^t h^t]^t,$ and $$a_2(k - [\![(p-1)/2]\!]) = F(p)x(k) + F(p-1)x(k-1) + \ldots$$

$$F(2)x(k-p+2) + F(1)x(k-p+1),$$

where $\{x_k, k=1,2,\ldots\}$ is the signal being analyzed, p is the number of points used in the parabolic fit (e.g. p=7), and dt is the time step of the signal being analyzed. Note that, for a fixed value of p, the filter coefficients F may be computed once and stored for later use in the computation of $a_2$ from the above FIR filter. The delay in computing $a_2$ at a given point, which is instilled by using $[\![(p-1)/2]\!]$ (i.e., the greatest integer less than or equal to (p−1)/2) future data points, is only (p+1)*dt/2 seconds. For example, with p=7 and dt=1/240, the delay is 1/60 sec.

Time-Weighted Averaging

In the methods described above, there are many cases in which it is desirable to compute some background or reference value for a particular signal. By accurately representing the history of the signal, one may improve the method's ability to identify relevant changes which standout from this background.

In this invention, time-weighted averaging is preferred. A subset of these techniques are able to determine a suitable long time-average of any desired functional of the input signal in a very computationally efficient manner, taking into account the entire recorded history of the signal and using only a minimal amount of computer memory. A particular example of the more general method is that of exponential forgetting, in which the recent signal information is weighted more heavily that the distant past.

The general form referred to as a time-weighted average of a continuous-time signal $\{X_t, t \geq 0\}$ with time-weight $\{f_{t,s}, t \geq 0, 0 \leq s \leq t\}$ is given by $\{m_t, t \geq 0\}$, where $$M_T = \frac{\int_0^T f_{t,s} X_s \, ds}{\int_0^T f_{t,s} \, ds}.$$

The discrete version of this time-average is obtained by simply replacing the integrals in the above definition by the corresponding summations over the index variable s. For certain time-weights, the above formula may be written recursively, in particular, this may be achieved for the case when f is independent of t. If the time-weight $f_{t,s}=e^{\lambda s}$, then a version of this time-weighted average can be simplified to the exponentially forgetting method that are employed in some of the embodiments of the invention described herein.

Variants on this choice may be useful for certain applications.

For example, by making $\lambda$ a periodic function of s with a period of one day, the time-weighted average may be used to weight signal information at a particular time of day more heavily than at other times. This may be particularly important for an individual who may commonly have seizure events only during certain times of day.

Also note that the choice of time-weight $f_{t,s}=X_{[t-\delta]}$ gives rise to the usual moving average $$m_t = \frac{1}{\delta} \int_{t-\delta}^{t} X_s \, ds,$$

Where X denotes the indicator function.

In the more general case of "time and state weighted averaging," the weight function, f, may also depend upon the signal X itself. This additional generalization incorporates the case in which the historical average not only depends on the epoch length over which the signal value is averaged, but also upon the signal value over this epoch. This technique may be useful when one desires to allow certain signal characteristics to, by their existence, modify the desired signal background average.

Having thus described the preferred embodiments of the present invention, the following is claimed as new and desired to be secured by Letters Patent:

1. A method of detecting the occurrence of abnormal activity in the brain of a subject, said method comprising the steps of:

(a) receiving into a signal processor input signals indicative of the subject's brain activity;

(b) determining ictal components in said input signals by applying to said input signals a first filter configured for extracting and enhancing ictal components from said input signals;

(c) measuring the ictal activity in a foreground epoch of said input signals by applying an order-statistic filter to said ictal components corresponding to said epoch to produce a foreground measure of said ictal activity;

(d) determining whether said foreground measure reaches a threshold level, such being indicative of the occurrence of said abnormal activity and (e) performing steps (a)–(d) while said abnormal activity is occurring before the onset of electroencephalographic waves of said abnormal activity.

2. The method as set forth in claim 1, step (b) including the step of using a digital filter as said first filter.

3. The method as set forth in claim 2, step (b) including the step of using a finite impulse response filter as said digital filter.

4. The method as set forth in claim 2, step (b) including the step of using an infinite impulse response filter as said digital filter.

5. The method as set forth in claim 1, step (b) including the step of using an analog filter as said first filter.

6. The method as set forth in claim 1, step (b) including the step of squaring the results of the application of said first filter to determine said ictal components.

7. The method as set forth in claim 1, step (c) including the step of measuring the ictal activity in a background epoch of said input signals by applying said order-statistic filter to said ictal components corresponding to said background epoch to produce a background measure of said ictal activity, said background epoch occurring before said foreground epoch, and step (d) including the step of determining whether the ratio of said foreground measure to said background measure reaches said threshold level.

8. The method as set forth in claim 7, step (c) including the step of configuring said foreground and background epochs to present a time delay therebetween.

9. The method as set forth in claim 8, step (c) including the step of configuring said foreground epoch as about two seconds, said background epoch as about twenty seconds and said delay as about one second.

10. The method as set forth in claim 7, step (c) including the step of continuously updating said foreground and background measures.

11. The method as set forth in claim 10, said threshold level being a first threshold level, step (c) including the step of suspending updating said background measure if said ratio reaches a second threshold level.

12. The method as set forth in claim 1, step (b) including the step of selecting said first filter from a filter bank including a plurality of filters configured for extracting and enhancing said ictal components.

13. The method as set forth in claim 12, step (b) including the step of selecting said first filter as the filter from said filter bank providing the greatest differentiation of ictal components.

14. The method as set forth in claim 13, said signal processor including memory means for storing said filter bank, step (b) including the step of retrieving a plurality of filters from said filter bank and applying said plurality of filters to said input signals in said signal processor and therein selecting said first filter as the filter from said plurality providing the greatest differentiation of ictal components.

15. The method as set forth in claim 1, further including the step of configuring said first filter in order to increase the differentiation of ictal components for the subject.

16. The method as set forth in claim 1, step (b) including the steps of using one of a finite impulse response filter and an infinite impulse response filter as said first filter, and squaring the results of the application of said first filter to enhance said ictal components, step (c) including the steps of measuring the ictal activity in a background epoch of said input signals by applying said order-statistic filter to said ictal components corresponding to said background epoch to produce a background measure of ictal activity and updating said foreground and background measures, said background epoch occurring before said foreground epoch and said foreground and background epochs presenting a time delay therebetween, and wherein said threshold level of step (d) is a first threshold level and step (c) further includes the step of suspending updating said background measure if said ratio reaches a second threshold level.

17. The method as set forth in claim 1, step (a) including the step of receiving said signals from at least one electrode operable for detecting the subject's brain activity and for producing said signals indicative thereof, said at least one electrode being selected from the group consisting of a scalp electrode and an implanted electrode.

18. The method as set forth in claim 1, step (a) including the step of receiving said signals from a memory device.

19. The method as set forth in claim 1, step (b) including the step of analyzing said signals in said signal processor selected from the group consisting of a microprocessor and a computer.

20. The method as set forth in claim 1, step (b) including the step of analyzing said signals in a signal processor implanted within the subject.

21. The method as set forth in claim 1, step (b) including the steps of analyzing said signals by using a wavelet filter as said first filter to determine corresponding wavelet coefficients of said signals, using said wavelet coefficients to determine a power density distribution, and comparing said power density distribution with said threshold level wherein the crossing of said threshold level by said distribution indicates the occurrence of said abnormal activity.

22. The method as set forth in claim 1, step (b) including the step of analyzing said signals using windowed Fourier and inverse Fourier transforms as said first filter.

23. The method as set forth in claim 1 including the step of producing an output in response to the indication of the occurrence of a seizure as said abnormal activity with said output taken from the group consisting of administering a medicament, electrically stimulating a portion of the subject's brain, magnetically stimulating a portion of the subject's brain, inhibiting activity in a portion of the subject's brain, electrically stimulating a nerve of the subject, recording said signals, activating an alert, stimulating physiological receptors of the patient, heating at least a portion of the subject's brain, cooling at least a portion of the subject's brain, facilitating activity in a portion of a subject's brain, disfacilitating activity in a portion of a subject's brain, and ablating a portion of the subject's brain.

24. The method as set forth in claim 23, further including the step of using a device implanted within the subject for producing said output.

25. The method as set forth in claim 1, said first filter being selected from a group consisting of a filter designed using random search algorithms, evolving algorithms, or genetic algorithms.

26. The method as set forth in claim 1, step (b) including the step of using a filter as said first filter taken from the group consisting of a digital filter, a nonlinear filter, an adaptive filter, a correlation integral, an arc length differential and a temperature filter.

27. The method as set forth in claim 1, said method including the step of detecting the occurrence of an epileptic seizure as said abnormal activity.

28. The method as set forth in claim 1 further including the step of receiving other biological signals concerning the subject into said processor and using said biological signals in detecting the occurrence of a seizure as said abnormal activity, said biological signals being representative of biological functions of the subject selected from the group consisting of respiratory activity and gases, concentrations of glucose, free radicals, indices of metabolic activity including metabolic by-products, electrolytes, neurotransmitters and other substances in blood, brain and/or other body tissues, brain temperature, intracranial pressure, blood flow, heart activity, muscle activity, ocular activity, magnetic fields, skin resistance and temperature, and electrical fields.

29. The method as set forth in claim 1, including the step of measuring said ictal activity in said foreground epoch against a background signal generated using time and state-weighted averaging of said input signals.

30. The method as set forth in claim 29, including the step of using an exponentially forgetting time averaging as said time and state-weighted averaging.

31. The method as set forth in claim 1, step (d) including the step of determining whether the magnitude of said foreground measure reaches said threshold level.

32. The method set forth in claim 1, further including the step of performing the method in portable apparatus connected to the subject.

33. The method as set forth in claim 1, wherein said threshold level is adaptive over time.

34. A method of predicting the occurrence of a seizure in the brain of a subject, said method comprising the steps of:
 (a) receiving into a signal processor input signals indicative of the subject's brain activity;
 (b) analyzing said signals for at least one precursor predictive of the occurrence of a seizure in the subject and
 (c) upon occurrence of said at least one precursor, producing an output in response before the onset of electroencephalographic waves signaling the occurrence of the seizure;
wherein step (b) includes the step of detecting epileptiform discharges in said signals, each discharge presenting a polarity, determining the sharpness of each of said discharges by determining a parabola of optimal fit for each of said discharges, determining an index of relative sharpness to the sharpness of other discharges by comparing each sharpness to the sharpness of other discharges in a time window, determining whether said index reaches a predetermined level, and determining whether said discharges reaching said predetermined level fit a predetermined pattern, such being predictive of a seizure.

35. The method as set forth in claim 34, step (b) including the step of determining said precursor by detecting epileptiform spikes by using a signal analysis filter to extract spike shape coefficients, determining a ratio of spike shape coefficients squared to background signal information, determining whether said ratio exceeds a predetermined level and, if so, determining whether spikes exceeding said ratio fit a pattern determined as being predictive of a seizure.

36. A method of predicting the occurrence of a seizure in the brain of a subject, said method comprising the steps of:
 (a) receiving into a signal processor input signals indicative of the subject's brain activity;
 (b) analyzing said signals for at least one precursor predictive of the occurrence of a seizure in the subject and
 (c) upon occurrence of said at least one precursor, producing an output in response before the onset of electroencephalographic waves signaling the occurrence of the seizure;
wherein step (b) includes the step of determining said precursor by determining a ratio of current signal energy compared to background energy and determining whether said ratio exceeds a predetermined level, such being predictive of a seizure.

37. A method of predicting the occurrence of a seizure in the brain of a subject, said method comprising the steps of:
 (a) receiving into a signal processor input signals indicative of the subject's brain activity;
 (b) analyzing said signals for at least one precursor predictive of the occurrence of a seizure in the subject and
 (c) upon occurrence of said at least one precursor, producing an output in response before the onset of electroencephalographic waves signaling the occurrence of the seizure;
wherein step (b) includes the step of determining said precursor by determining a ratio of median frequency to background median frequency and determining whether said ratio exceeds a predetermined level, such being predictive of a seizure.

38. A seizure detection, prediction and treatment apparatus for detecting the occurrence of a seizure in the brain of a subject, comprising:
 receiving means for receiving input signals indicative of the subject's brain activity;
 signal processing means coupled with said receiving means to:
  determine ictal components in said input signals by applying to said input signals a first filter configured to extract and enhance ictal components from said input signals,
  measure the ictal activity in a foreground epoch of said input signals by applying an order-statistic filter to said ictal components corresponding to said epoch to produce a foreground measure of ictal activity, and
  determine whether said foreground measure exceeds a predetermined level, such being indicative of the occurrence of a seizure; and
 output means for producing an output before the onset of electroencephalographic waves of said input signals indicating the impending occurrence of the seizure.

39. The apparatus as set forth in claim 38, wherein said predetermined level has a selected magnitude.

40. The apparatus as set forth in claim 38, wherein said predetermined level is an adaptive threshold.

41. A method of detecting the occurrence of abnormal activity in the brain of a subject, said method comprising the steps of:
 (a) receiving into a signal processor input signals indicative of the subject's brain activity;
 (b) determining at least one ictal component in said input signals;
 (c) measuring the ictal activity indicated by said at least one ictal component in a foreground epoch of said input signals to produce a foreground measure of said ictal activity;
 (d) determining whether said ictal activity of said foreground measure is indicative of the occurrence of said abnormal activity; and (e) performing steps (a)–(d) while said ictal activity is occurring before the onset of electroencephalographic wave signals of said abnormal activity.

42. The method as set forth in claim 41 further including the step of providing information to the subject regarding the at least one ictal component and/or at least one non-ictal component of the input signals for the purpose of initiating biofeedback to the subject indicative of a selected activity state of the brain of the subject.

43. The method as set forth in claim 42, wherein said activity state is selected from the group consisting of a seizure or epileptiform discharge.

44. The method as set forth in claim 41, step (b) including the step of applying to said input signals a first filter configured for extracting from, and enhancing said at least one ictal component of, said input signals.

45. The method as set forth in claim 41, step (c) including the step of applying an order-statistic filter to said at least one ictal component corresponding to said epoch to produce said foreground measure of ictal activity.

46. The method as set forth in claim 41, step (d) including the step of determining whether said ictal activity reaches a threshold level indicative of the occurrence of said abnormal activity.

47. The method as set forth in claim 41, step (d) including the step of determining whether said ictal activity reaches an adaptive threshold level over time indicative of the occurrence of said abnormal activity.

48. The method as set forth in claim 41, step (e) including the step of performing steps (a)–(d) before the onset of a selected clinical component indicative of the occurrence of said abnormal activity.

49. The method as set forth in claim 41,
step (c) including the step of measuring the ictal activity of said at least one ictal component in a background epoch of said input signals to produce at least one background measure of ictal activity, said background epoch occurring before said foreground epoch, and
step (d) including the step of determining whether a ratio of said at least one foreground measure to said at least one background measure reaches a threshold level indicative of said occurrence of said abnormal activity.

50. The method as set forth in claim 41, step (e) including the step of performing steps (a)–(d) before the onset of a selected at least one biological signal indicative of the occurrence of said abnormal activity, said at least one biological signal being representative of a respective biological function of the subject selected from the group consisting of respiratory activity and gases, concentrations of glucose, free radicals, indices of metabolic activity including metabolic by-products, electrolytes, neurotransmitters and other substances in blood, brain and/or other body tissues, brain temperature, intracranial pressure, blood flow, heart activity, muscle activity, ocular activity, magnetic fields, skin resistance and temperature, and electrical fields.

51. A method of detecting the occurrence of abnormal activity in the brain of a subject, said method comprising the steps of:

(a) receiving into a signal processor input signals indicative of the subject's brain activity;

(b) determining at least one ictal component in said input signals;

(c) measuring the ictal activity indicated by said at least one ictal component in a foreground epoch of said input signals to produce a foreground measure of said ictal activity;

(d) determining whether said ictal activity of said foreground measure is indicative of the occurrence of said abnormal activity; and (e) performing steps (a)–(d) while said abnormal activity is occurring before the onset of electrocorticogram wave signals of said abnormal activity.

52. The method as set forth in claim 51, step (e) including the step of performing steps (a)–(d) before the onset of a clinical component indicative of the occurrence of said abnormal activity.

* * * * *

UNITED STATES PATENT AND TRADEMARK OFFICE
CERTIFICATE OF CORRECTION

PATENT NO.   : 5,995,868
DATED        : November 30, 1999
INVENTOR(S)  : Josef Dorfmeister et al.

It is certified that error appears in the above-identified patent and that said Letters Patent is hereby corrected as shown below:

Title page,
Immediately below "United States Patent" delete "Dorfmeister et al." and replace with -- Osorio et al. --

Item [75], Inventors, delete the information provided and replace with -- Ivan Osorio, Leawood; Mark Frei; David Lerner; John Ralston; Josef Dorfmeister, all of Lawrence, all of Kansas. --

Column 26,
Line 56, in the equation, insert -- = -- between "½" and between "50%".
Line 61, delete "15".

Column 29,
Line 14, in the equation, insert -- = -- between "$B_i$" and "$\sum_{k=1}^{n}$".

Column 30,
Line 38, replace "$X_{[t-\delta]}$" with -- $X_{[t,t-\delta]}$ --.

Signed and Sealed this

Fifth Day of February, 2002

JAMES E. ROGAN
*Director of the United States Patent and Trademark Office*

*Attest:*

*Attesting Officer*